US006303116B1

(12) United States Patent
Dornburg

(10) Patent No.: US 6,303,116 B1
(45) Date of Patent: Oct. 16, 2001

(54) GENETICALLY ENGINEERED RETROVIRAL VECTOR PARTICLES CAPABLE OF INFECTING NON-DIVIDING CELLS

(75) Inventor: Ralph Dornburg, Philadelphia, PA (US)

(73) Assignee: Thomas Jefferson University, Phila, PA (US)

(*) Notice: Subject to any disclaimer, the term of this patent is extended or adjusted under 35 U.S.C. 154(b) by 0 days.

(21) Appl. No.: 09/496,379

(22) Filed: Feb. 2, 2000

Related U.S. Application Data

(60) Provisional application No. 60/118,281, filed on Feb. 2, 1999.

(51) Int. Cl.[7] ........................ A61K 48/00; C12N 15/867; C12N 15/63; C12N 15/64

(52) U.S. Cl. ........................ 424/93.2; 424/93.1; 424/93.6; 435/320.1; 435/235.1; 435/91.1; 435/91.4; 435/91.33; 435/455; 435/456

(58) Field of Search .............................. 435/320.1, 235.1, 435/91.1, 91.4, 91.33, 455, 456; 424/93.1, 93.2, 93.6

(56) References Cited

U.S. PATENT DOCUMENTS 5,576,201 * 11/1996 Mason et al. ........................ 435/456

OTHER PUBLICATIONS

Chu, T., and Dornburg, R., "Toward Highly Efficient Cell–Type–Specific Gene Transfer with Retroviral Vectors Displaying Single–Chain Antibodies", *J. Virology*, 71:1: 720–725, Jan. 1997.

Chu, T., and Dornburg, R., "Retroviral Vector Particles Displaying the Antigen–Binding Site of an Antibody Enable Cell–Type–Specific Gene Transfer", *J. Virology*, 69:4: 2659–2663, Apr. 1995.

Nilson, B.H.K., et al., "Targeting of Retroviral Vectors Through Protease–Substrate Ineraction", *Gene Therapy*, 3:280–286, 1996.

Koo, H.M., et al., "Spleen Necrosis Virus, an Avian Retrovirus, Can Infect Primate Cells", *J. Virology*, 65:9: 4769–4776, Sep. 1991.

Martinez, I., And Dornburg, R., "Improved Retroviral Packaging Lines Derived from Spleen Necrosis Virus", *Virology*, 208: 234–241, 1995.

Mikawa, T., et al., "In Vivo Analysis of a New IacZ Retrovirus Vector Suitable for Cell Lineage Marking in Avian and Other Species", *Experimental Cell Research*, 195: 516–523, 1991.

Gautier, R., et al., "Avian Reticuloendotheliosis Virus Strain A and Spleen Necrosis Virus Do Not Affect Infect Human Cells", *J. Virology*, 74:1: 518–522, Jan. 2000.

Jiang, A., et al., "Cell–Type–Specific Gene Transfer into Human Cells with Retroviral Vectors that Display Single–Chain Antibodies", *J. Virology*, 72:12: 10148–10156, Dec. 1998.

Engelstädter, M., et al., "Targeting Human T Cells by Retroviral Vectors Displaying Antibody Domains Selected from a Phage Display Library", *Human Gene Therapy*, 11: 293–303, Jan. 20, 2000.

Koo, H.M., et al., "Retriculoendotheliosis Type C and Primate Type D Oncoretroviruses Are Members of the Same Receptor Interference Group", *J. Virology*, 66:6: 3448–3454, Jun. 1992.

Kewalramani, V.N., et al., "Spleen Necrosis Virus, an Avian Immunosuppresive Retrovirus, Shares a Receptor with the Type D Simian Retroviruses", *J. Virology*, 66:5: 3026–3031, May 1992.

Butsch, M., et al., "The 5' RNA Terminus of Spleen Necrosis Virus Contains a Novel Posttranscriptional Control Element That Facilitates Human Immunodeficiency Virus Rev/RRE–Independent Gag Production", *J. Virology*, 73:6: 4847–4855, Jun. 1999.

Schnierle, B.S., et al., "Expression of Chimeric Envelope Proteins in Helper Cell Lines and Integration into Moloney Murine Leukemia Virus Particles", *Gene Therapy*, 3: 334–342, 1996.

Dornburg, R., "Reticuloendotheliosis Viruses and Derived Vectors", *GeneTherapy*, 2: 301–310, 1995.

* cited by examiner

*Primary Examiner*—David Guzo
(74) *Attorney, Agent, or Firm*—Janet B. Smith

(57) ABSTRACT

The present invention is a method of generating retroviral vector particles derived from retroviruses and capable of transducing therapeutic genes into non-dividing cells.

4 Claims, 14 Drawing Sheets

| aa position | 25 | 26 | 27 | 28 | 29 | 30 |
|---|---|---|---|---|---|---|
| **HIV-1-NLS (concensus)** | **gly** | **lys** | **lys** | *lys* | **tyr** | *lys* |
| **HIV-1 (brain isolate)** | **gly** | **lys** | **lys** | *gln* | **tyr** | *arg* |

| aa position | 24 | 25 | 26 | 27 | 28 | 29 |
|---|---|---|---|---|---|---|
| **SNV (wild-type)** | phe | **lys** | **lys** | *arg* | ala | gly |
| **SNV-m1** | **gly** | **lys** | **lys** | *arg* | ala | gly |
| **SNV-m2** | phe | **lys** | **lys** | **lys** | ala | gly |
| **SNV-m3** | phe | **lys** | **lys** | *arg* | **tyr** | gly |
| **SNV-m4** | phe | **lys** | **lys** | *arg* | ala | **lys** |

| | | | | | | |
|---|---|---|---|---|---|---|
| **SNV-m5** | **gly** | **lys** | **lys** | *arg* | **tyr** | gly |
| **SNV-m5b** | **gly** | **lys** | **lys** | **lys** | **tyr** | gly |
| **SNV-m6** | **gly** | **lys** | **lys** | *arg* | ala | **lys** |
| **SNV-m7** | phe | **lys** | **lys** | *arg* | **tyr** | **lys** |
| **SNV-m8** | **gly** | **lys** | **lys** | **lys** | **tyr** | **lys** |

Fig. 2

SEQUENCE LISTING

```
<160> NUMBER OF SEQ ID NOS:  12

<210> SEQ ID NO 1
<211> LENGTH: 6
<212> TYPE: PRT
<213> ORGANISM: Artificial Sequence
<220> FEATURE:
<223> OTHER INFORMATION: matrix protein of wt SNV

<400> SEQUENCE: 1

Phe Lys Lys Arg Ala Gly
 1               5


<210> SEQ ID NO 2
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 2

Gly Lys Lys Arg Ala Gly
 1               5


<210> SEQ ID NO 3
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 3

Phe Lys Lys Lys Ala Gly
 1               5


<210> SEQ ID NO 4
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 4

Phe Lys Lys Arg Tyr Gly
 1               5


<210> SEQ ID NO 5
<211> LENGTH: 6
<212> TYPE: PRT
<213> ORGANISM: Artificial Sequence
<220> FEATURE:
```

-continued

```
<223> OTHER INFORMATION: matrix protein mutation to NLS

<400> SEQUENCE: 5

Phe Lys Lys Arg Ala Lys
 1               5


<210> SEQ ID NO 6
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 6

Gly Lys Lys Arg Tyr Gly
 1               5


<210> SEQ ID NO 7
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 7

Gly Lys Lys Lys Tyr Gly
 1               5


<210> SEQ ID NO 8
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 8

Gly Lys Lys Arg Ala Lys
 1               5


<210> SEQ ID NO 9
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 9

Phe Lys Lys Arg Tyr Lys
 1               5


<210> SEQ ID NO 10
<211> LENGTH: 6
<212> TYPE: PRT
<213> ORGANISM: Artificial Sequence
<220> FEATURE:
<223> OTHER INFORMATION: matrix protein mutation to NLS

<400> SEQUENCE: 10

Gly Lys Lys Lys Tyr Lys
 1               5


<210> SEQ ID NO 11
<211> LENGTH: 6
<212> TYPE: PRT
<213> ORGANISM: Artificial Sequence
<220> FEATURE:
<223> OTHER INFORMATION: HIV-1 NLS (consensus)
```

-continued

```
<400> SEQUENCE: 11

Gly Lys Lys Lys Tyr Lys
 1               5


<210> SEQ ID NO 12
<211> LENGTH: 6
<212> TYPE: PRT
<213> ORGANISM: Artificial Sequence
<220> FEATURE:
<223> OTHER INFORMATION: HIV-1 brain isolate NLS

<400> SEQUENCE: 12

Gly Lys Lys Gln Tyr Arg
 1               5
```

GENETICALLY ENGINEERED RETROVIRAL VECTOR PARTICLES CAPABLE OF INFECTING NON-DIVIDING CELLS

CROSS REFERENCE TO RELATED APPLICATIONS

This application claims priority in part under 35 U.S.C. §119(e) based upon U.S. Provisional Patent Application No. 60/118,281, filed Feb. 2, 1999.

FIELD OF THE INVENTION

This invention generally relates to the field of virology, and, more particularly, to a system of generating and producing retroviral vector particles from retroviruses which are non-pathogenic for humans and capable of transducing therapeutic genes into non-dividing cells.

BACKGROUND OF THE INVENTION

All current retroviral vectors used in human gene therapy protocols have been derived from murine leukemia virus (MLV), an amphotropic C-type retrovirus. However, like all other C-type retroviruses, MLV can only establish an infection in the target cell after one cell division. To bypass this problem, efforts are underway in several laboratories to develop retroviral vectors from lentiviruses, such as the human immunodeficiency virus (HIV-1) the major causative agent of AIDS, which are capable of infecting non-dividing cells. However, serious safety issues make it highly unlikely that such vectors could be used in the clinic.

The present invention describes procedures for the generation and production of safe retroviral vectors derived from C-type retroviruses, which are non-pathogenic for humans and which are capable of transducing genes into specific non-dividing cells. Transduction of genes into non-dividing cells has been achieved in the present invention by using the approaches described herein. Using site-directed mutagenesis, a specific signal (nuclear transportation signal sequence) has been introduced into the matrix protein of the retroviral vector particle. This signal is sufficient to enable the penetration of the nucleus of the non-dividing cell.

The introduction of a nuclear localization sequence into the matrix protein adds a new feature to the C-type retroviral vector particle: the capability to actively penetrate the nucleus of a quiescent cell. This system has two major advantages over current vector systems. First, efficient gene transfer into non-dividing cells is achieved. Moreover, this system is, but does not have to be, combined with an existing cell-type-specific gene delivery system. Second, this system is safe, since the retroviral particles used have been derived from a retrovirus which is non-pathogenic in humans.

DEFINITIONS

"Nuclear translocation sequence" means nuclear localiation sequence or nuclear transportation signal sequence.

SUMMARY OF THE INVENTION

The retroviral vector system described here may be used to deliver genes into various tissues of the human body, which consists of non-dividing cells, e.g., liver, hematopoietic stem cells, brain and many more cell-types. It can be combined with a cell-type-specific gene delivery system developed by us earlier to transfer genes into a very distinctive cell-type only. Thus, there will be numerous human gene therapy applications into various organs transducing a large variety of therapeutic genes. The system described here overcomes the last major hurdle and disadvantage of current retroviral vector systems, which is the incapability to infect non-dividing cells.

This invention also relates to a method for preparing particles, which contain genetically modified core proteins involved in the import of retroviral cores into the nucleus.

The present invention describes procedures for the generation and production of safe retroviral vectors derived from retroviruses, which are non-pathogenic for humans and capable of transducing genes into non-dividing cells. This has been achieved using the following approaches. Using site-directed mutagenesis, a specific signal (nuclear transportation signal sequence); FIG. 2 and SEQ. ID. NO: 1–10 has been introduced into the core protein of the retroviral vector particle. This signal is sufficient to enable the penetration of the nucleus of the non-dividing cell.

In one embodiment, the present invention pertains to a C-type retroviral vector particle having a genetically modified MA core protein, wherein a consensus nuclear translocation sequence (HIV-1 census sequence, SEQ. ID. NO: 11) has been created by altering the amino acid sequence of the wild-type core protein.

In another embodiment, the present invention pertains to a method for preparing a C-type retroviral particle having the capability to infect quiescent cells which comprises a retroviral vector core particle which contains a genetically engineered MA protein wherein a nuclear translocation sequence has been created by altering the amino acid sequence of the wild-type MA protein.

In yet another embodiment, the present invention pertains to a C-type retroviral particle having the capability to infect quiescent cells which comprises a retroviral vector core particle which contains a genetically engineered MA protein, wherein a nuclear translocation sequence has been created by altering the amino acid sequence of the wild-type MA protein, which facilitates nucleus penetration of the infected target cell.

In yet another embodiment, the present invention pertains to a method for preparing a C-type retroviral particle having the capability to infect quiescent cells which comprises a retroviral vector core particle which contains a genetically engineered MA protein wherein a nuclear translocation sequence has been created by altering the amino acid sequence of the wild-type MA protein, which facilitates nucleus penetration of the infected target cell.

DESCRIPTION OF THE DRAWINGS

FIG. 2 illustrates a consensus nuclear translocation sequence of HIV-1 (SEQ. ID. NO: 11) as well as HIV-1 nuclear translocation sequence of an individual HIV-1 strain (isolated from quiescent human brain cells) (SEQ. ID. NO:

12). Below are the amino acid sequences of SNV at the some position in MA as in HIV-1 (SEQ. ID. NO: 11) and mutations introduced into this region using site directed mutagenesis (SEQ. ID. NO: 2–10). Three mutations generate a nuclear translocation sequence in the MA protein of SNV. The figure shows all single, double, and triple mutations, termed SNV-MA-mut1, 2, 3, etc (SEQ. ID. NO: 2, 3, 4, ect., respectively). The effect of each single, double, and the final triple mutations (e.g., SNV-MA-mut7); (SEQ. ID. NO: 9) has been tested individually for efficiency of replication and the ability to infect quiescent cells.

Figure 3:
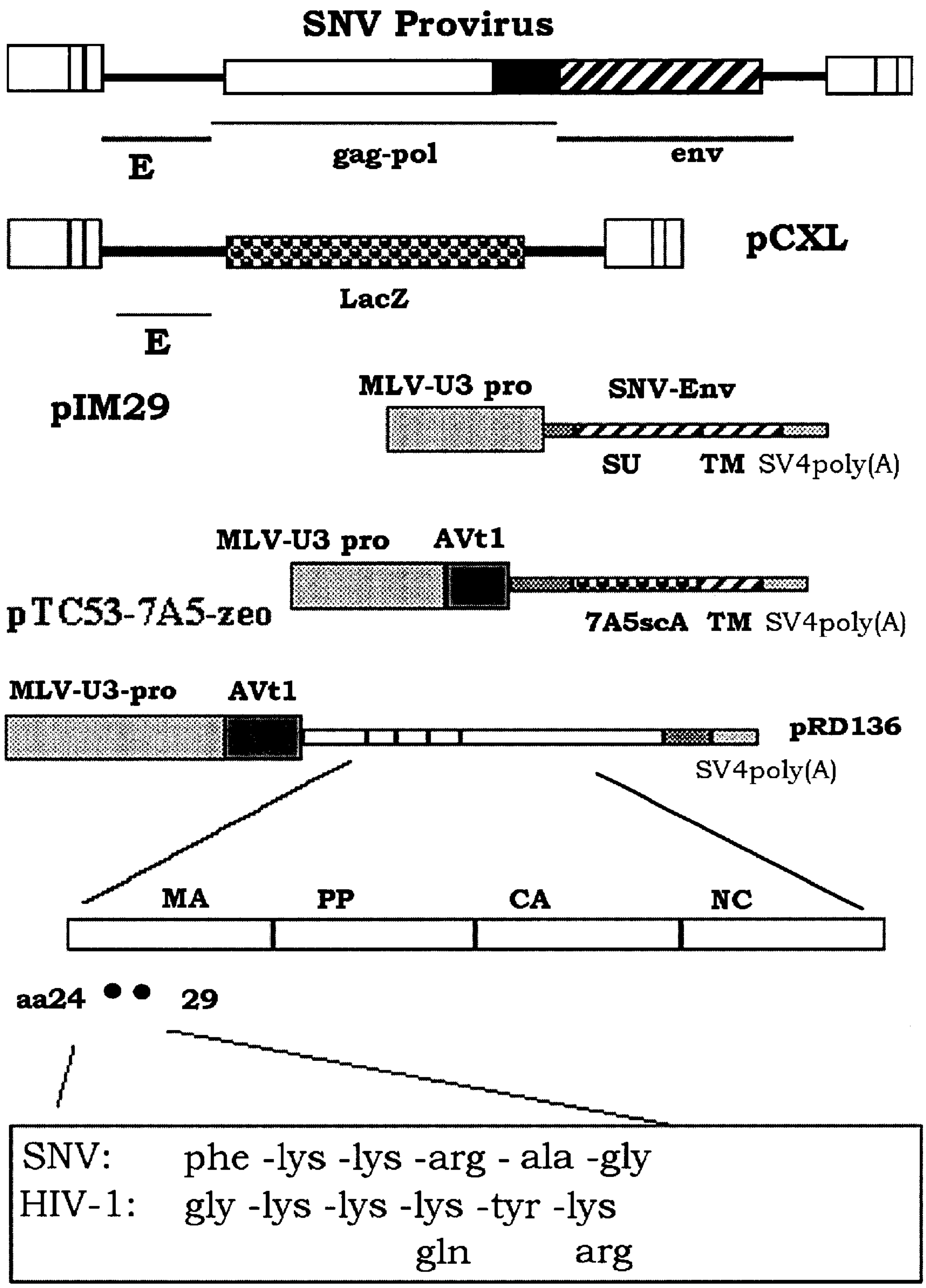

FIG. 3(parts A–B). illustrates the plasmids used to express retroviral protein or to introduce a retroviral vector into packaging cells. An SNV retrovirus provirus is shown at the top. It has the genomic organization typical for a C-type retrovirus. The retroviral vector pCXL contains the bacterial beta-galactosidase gene in place of the retroviral protein coding sequences. pIM29 is a plasmid vector for the expression of the SNV wild-type envelope gene. The env gene is expressed from the murine leukemia virus (MLV) U3 promoter (MLV-U3-pro). Polyadenylation is ediated by the simian virus 40 (SV40) polyadenylation signal sequence SV40polyA). pTC53-7A5zeo expresses a chimeric single chain antibody-envelope scA-Env) fusion protein. The scA recognizes a cell surface protein expressed on various human hematopoietic cells, e.g., T-lymphocytes and macrophages (Engelstädter, M., et al. Targeting human T-cells by retroviral vectors displaying antibody domains selected from a phage display library, 1999 (submitted for publication). The plasmid construct is similar to pIM29. It contains the adenovirus tripartite leader sequence (AVt1) downstream of the MLV-U3 promoter for enhance gene expression. pRD136 is similar to plasmid pTC53-7A5zeo. It expresses the SNV wild-type gag-pol proteins. The location of the MA sequence, which has been mutated, is indicated at bottom and compared to the NLS sequence of HIV-1 (SEQ. ID. NO: 11) (for more details see FIG. 2). E: encapsidation sequence.

Figure 4:
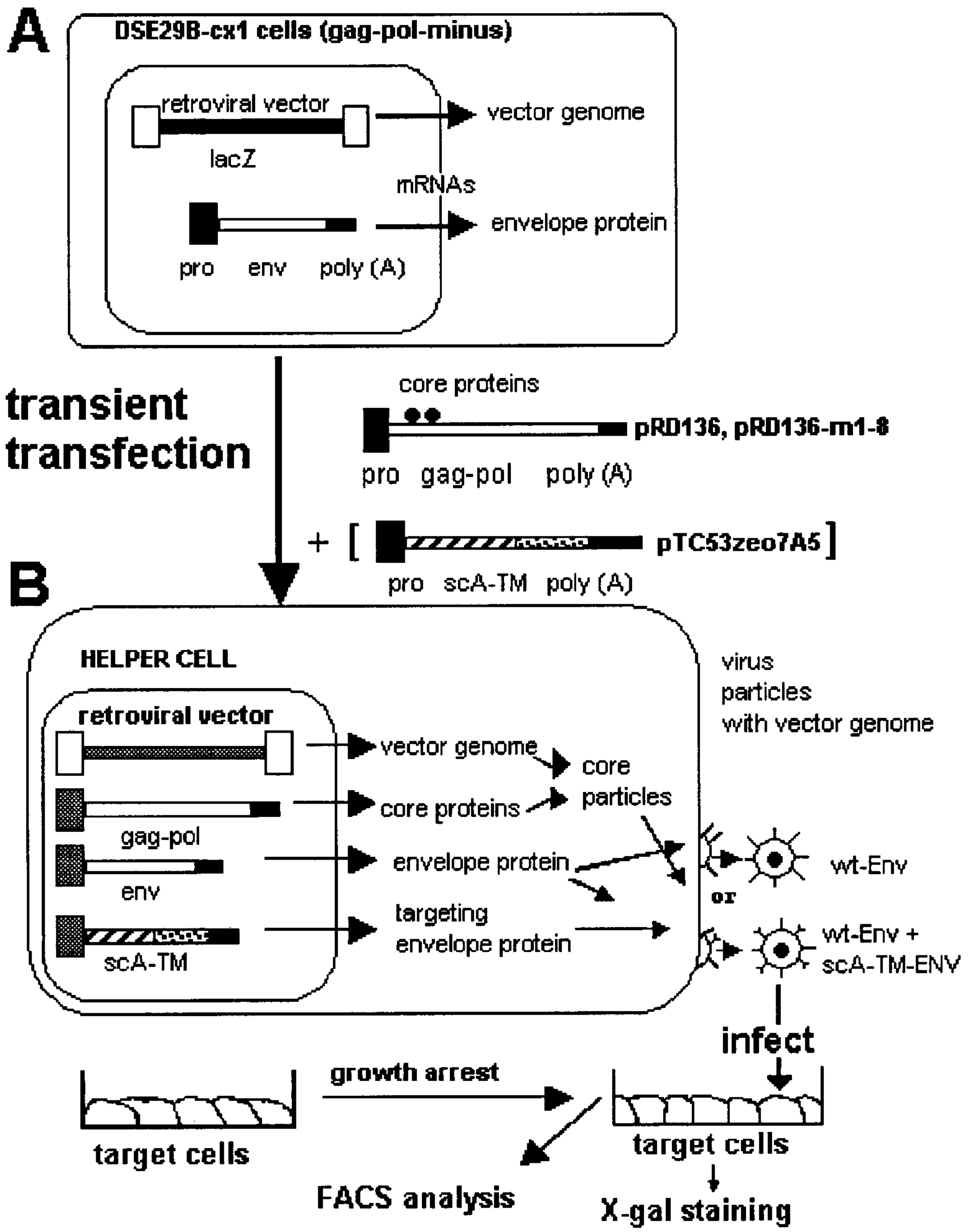
Figure 5A:
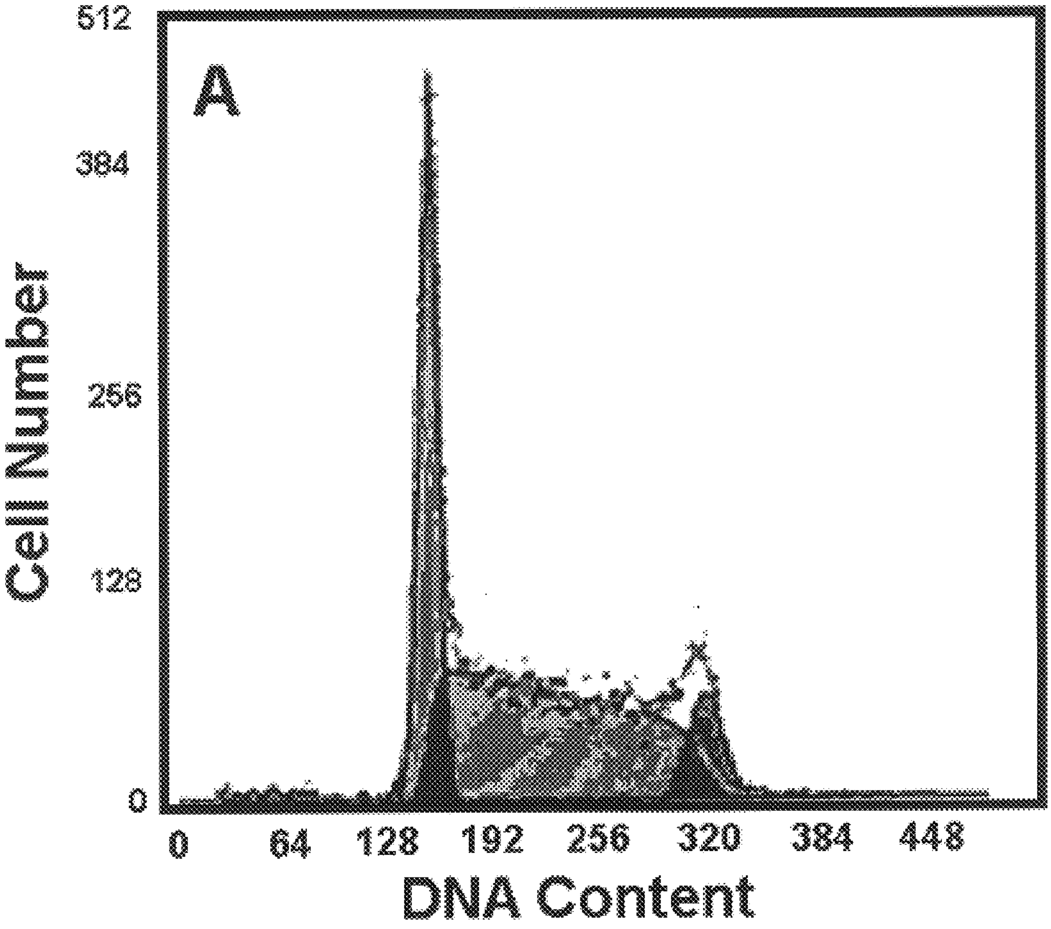
Figure 5B:
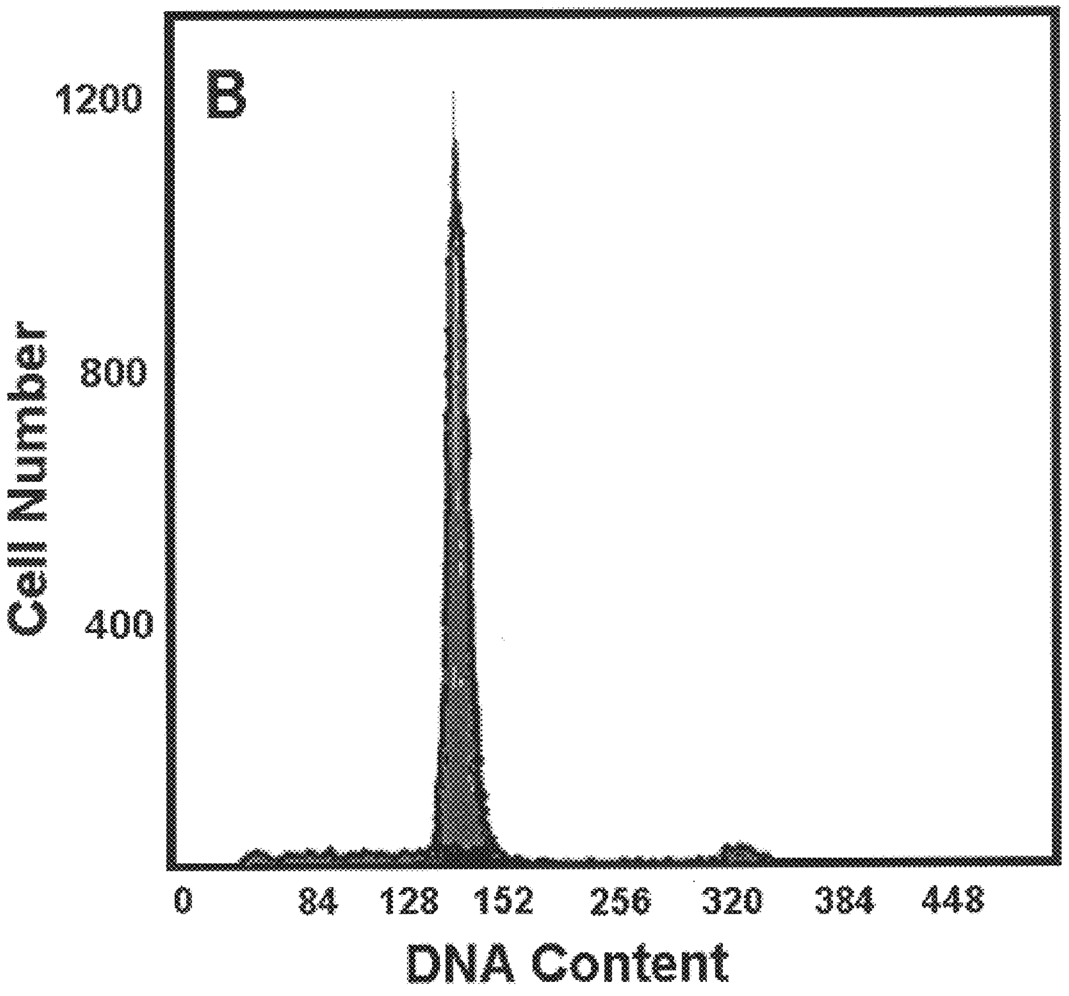
Figure 5C:
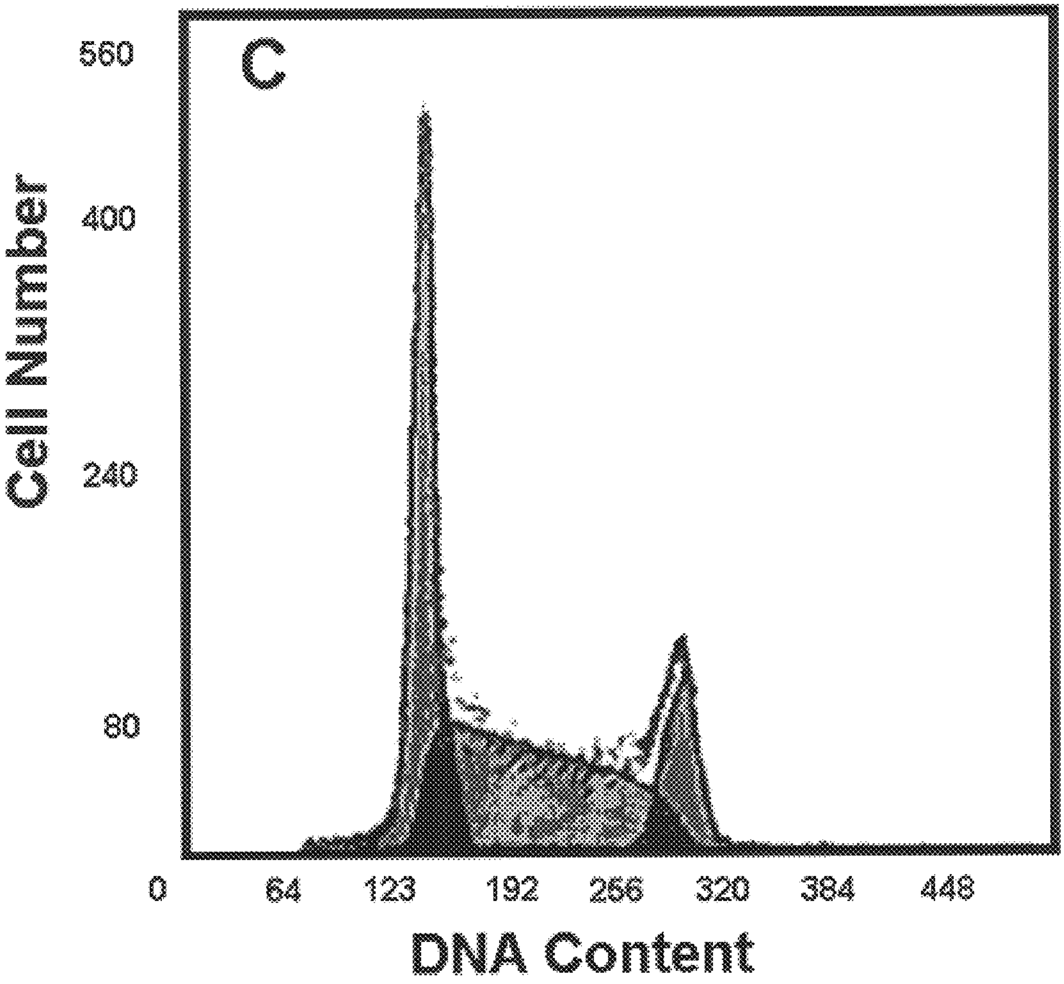
Figure 5D:
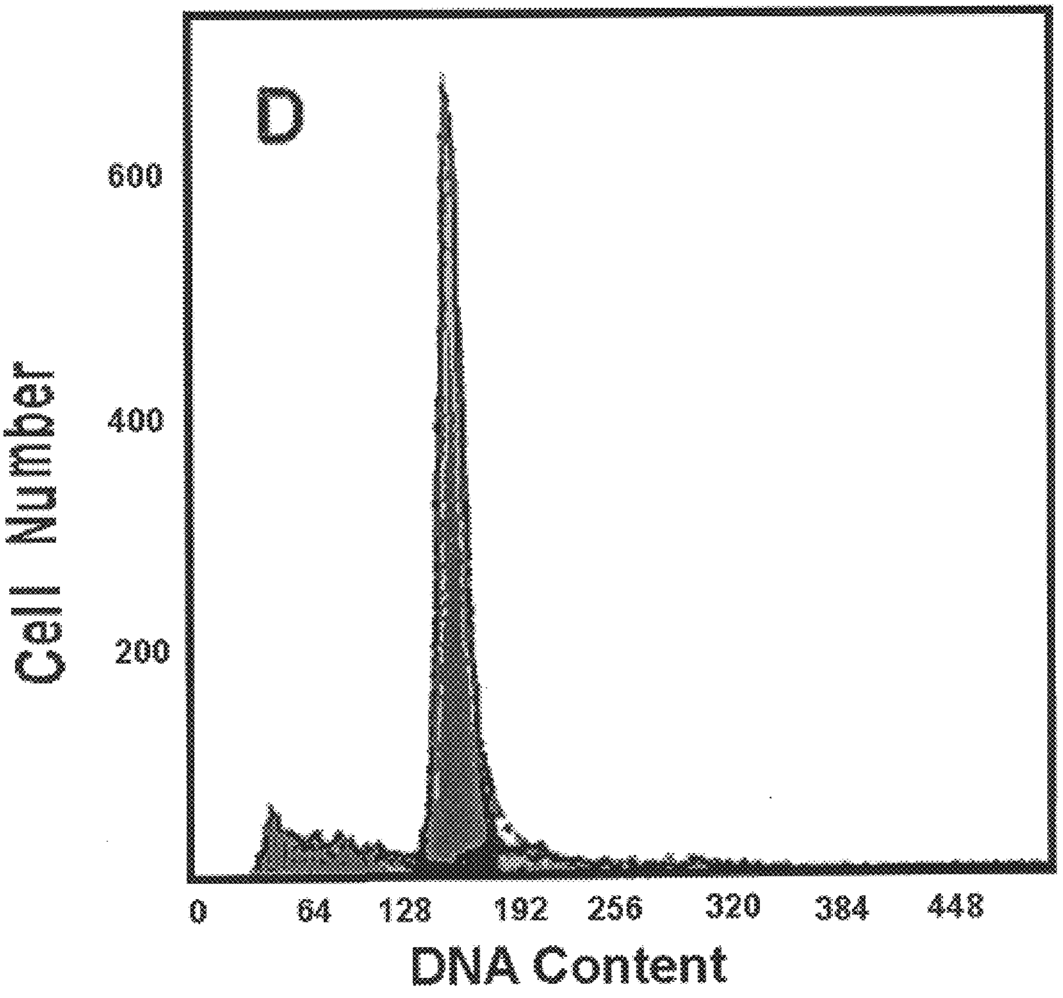

FIG. 4 illustrates the protocol used to test whether mutations in the MA protein of a retrovirus would interfere or hamper retrovirus replication and whether the mutations would enable the infection of quiescent cells. A cell line was made which expresses the envelope protein of a retrovirus (e.g., SNV) and a retroviral vector transducing the bacterial β-galactosidase gene (the cell line was termed DSE29-cxl). Transfection of a construct expressing wild-type or mutant Gag-Pol generates a complete retroviral packaging line (SEQ. ID. NO: 10, 11 and 12). Virus was harvested from such cell lines and fresh target cells were infected.

FIG. 5(parts A–D). FACS analysis of the DNA content of D17 or C8166 cells. Examples of flow cytometry patterns of cells stained with propidium-iodide. A: proliferating D17 cells: B: D17 cells growth-arrested with mitomycin for 36 hours. C: proliferating C8166 cells; D: C8166 cells growth arrested with mitomycin for 36 hours.

Figure 6A:
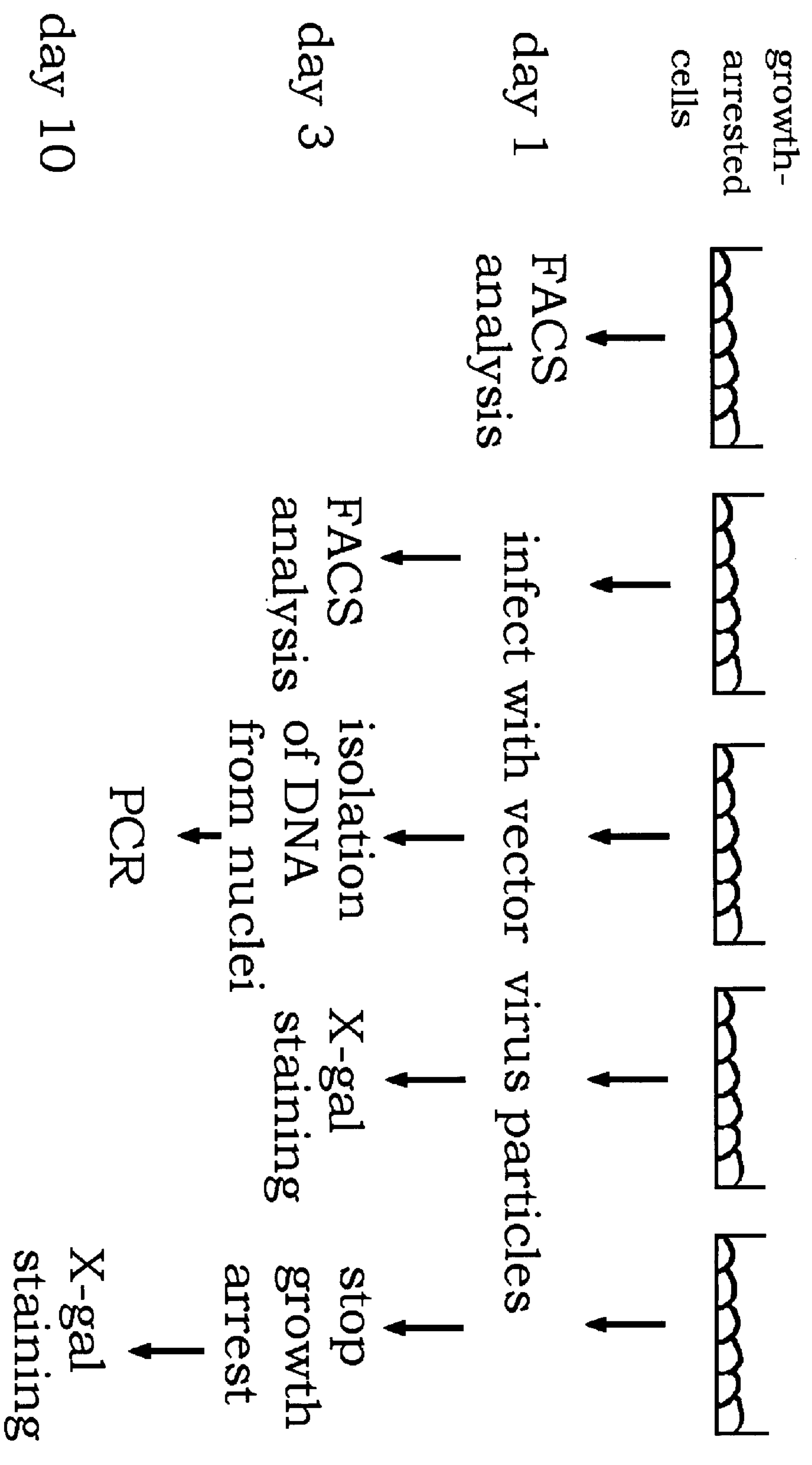
Figure 6B:
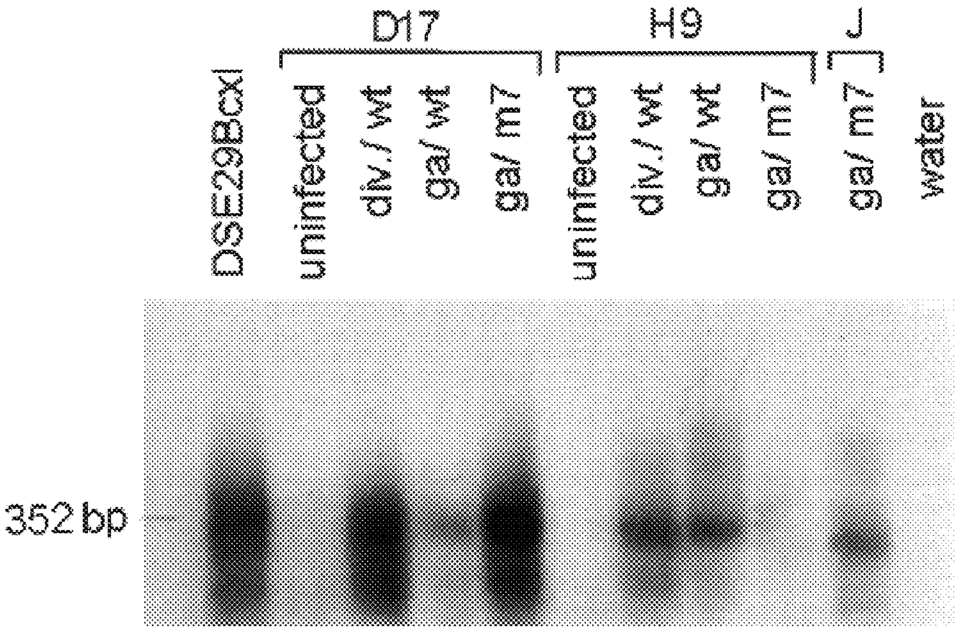

FIG. 6(parts A–B). Experiments to test for the presence of viral DNA in the nuclei of infected quiescent cells. A) Experimental protocol. Target cells (dog D17 cells, human H9 or Jurkat cells) were growth-arrested with mitomycin. At day 1, an aliquot of the cells was subjected to FACS analysis to verify the growth arrest. Four other aliquots were infected with vector virus particles containing wt or mutant (pRD136-m7) MA proteins. Two days after infection, another aliquot of the cells was subjected to FACS analysis to verify the maintenance of the growth-arrested state of the cells. DNA was isolated from the nuclei of one aliquot, another aliquot was stained with X-gal to verify efficient infection. The last aliquot was kept in tissue culture without mitomycin and cells were stained with X-gal to test for integration, e.g., stable gene expression after another week. B) Southern blot analysis of PCR products. DNA isolated from the nuclei of growth-arrested or dividing cells was subjected to PCR with primers specific for the lacZ gene. PCR products were subjected to agarose gel electrophoresis, the DNA was transferred to a nitrocellulose filter (Southern blot), and hybridized with a 32P-labelled lacZ-specific probe. div.=dividing; ga=growth-arrested; wt=vector particles containing wt MA; m7=vector particles containing the pRD136-m7 mutant MA protein. J=jurkat cells.

FIG. 7(parts A–D). Infection of human blood monocyte-derived macrophages. Infection with particles containing A: wt-MA and wt-Env; B: wt-MA, wt-+targeting-Env; C: MA derived from RD136-m7 and wt-Env; D: MA derived from RD136-m7, wt-+targeting-Env.

DETAILED DESCRIPTION

This invention relates to genetically engineered retroviral vector particles capable of transducing genes into non-dividing cells. The genetically engineered retroviral vector particle contains a mutant core protein containing a nuclear translocation sequence involved in the active import of the retroviral core (pre-integration complex) into the nucleus of the infected target cell.

Retroviruses are wide-spread in nature and are associated with various diseases in animals and man. (Varmus, H. E. and P. Brown. 1988. Retroviruses, p. 53–108. In D. E. Berg and M. M. Howe (eds.), Mobile DNA. American Society for Microbiology, Washington, D.C.). They contain an RNA genome, which is converted into a double-stranded DNA copy. This DNA copy is inserted into the genome of the host cell. Thus, a retrovirus becomes part of the genomic outfit of the infected cell. Some retroviruses carry non-retroviral genes, which have been acquired from the infected cell by recombination. Thus, retroviruses act as natural gene transfer vectors. These features, as well as the high efficiency of this process, has led to the construction of retroviral vectors useful for the transfer of many non-retroviral genes into a large variety of different cells (Dornburg, R., *Gene Ther.*, 2:301–310, 1995; Eglitis, M. A. and Anderson, W. F., *Biotechniq.*, 6:608–614, 1988; Miller, A. D., *Hum. Gene. Ther.*, 1:5–14, 1990). In recent years, retroviral vectors have been also used to transfer therapeutic genes into human cells to cure genetic diseases, cancer, AIDS, and various other diseases. (Anderson, W. F., *Nature* 392:25–30, 1998).

All current retroviral vectors used in clinical trials have been derived from murine leukemia virus (MLV), a C-type retrovirus, which is considered non-pathogenic for humans. MLV has a rather simple genomic organization. It contains only two gene units, which code for the inner core structure proteins and the envelope protein, respectively. It does not contain regulatory genes like HIV-1. Thus, the construction of safe gene delivery systems is rather simple and straightforward. (FIG. 1) Such delivery systems consist of two components: the retroviral vector, which is a genetically modified viral genome that contains the gene of interest replacing retroviral protein coding sequences, and a helper cell that supplies the retroviral proteins for the encapsulation of the vector genome into retroviral particles (FIG. 1).

Figure 1:
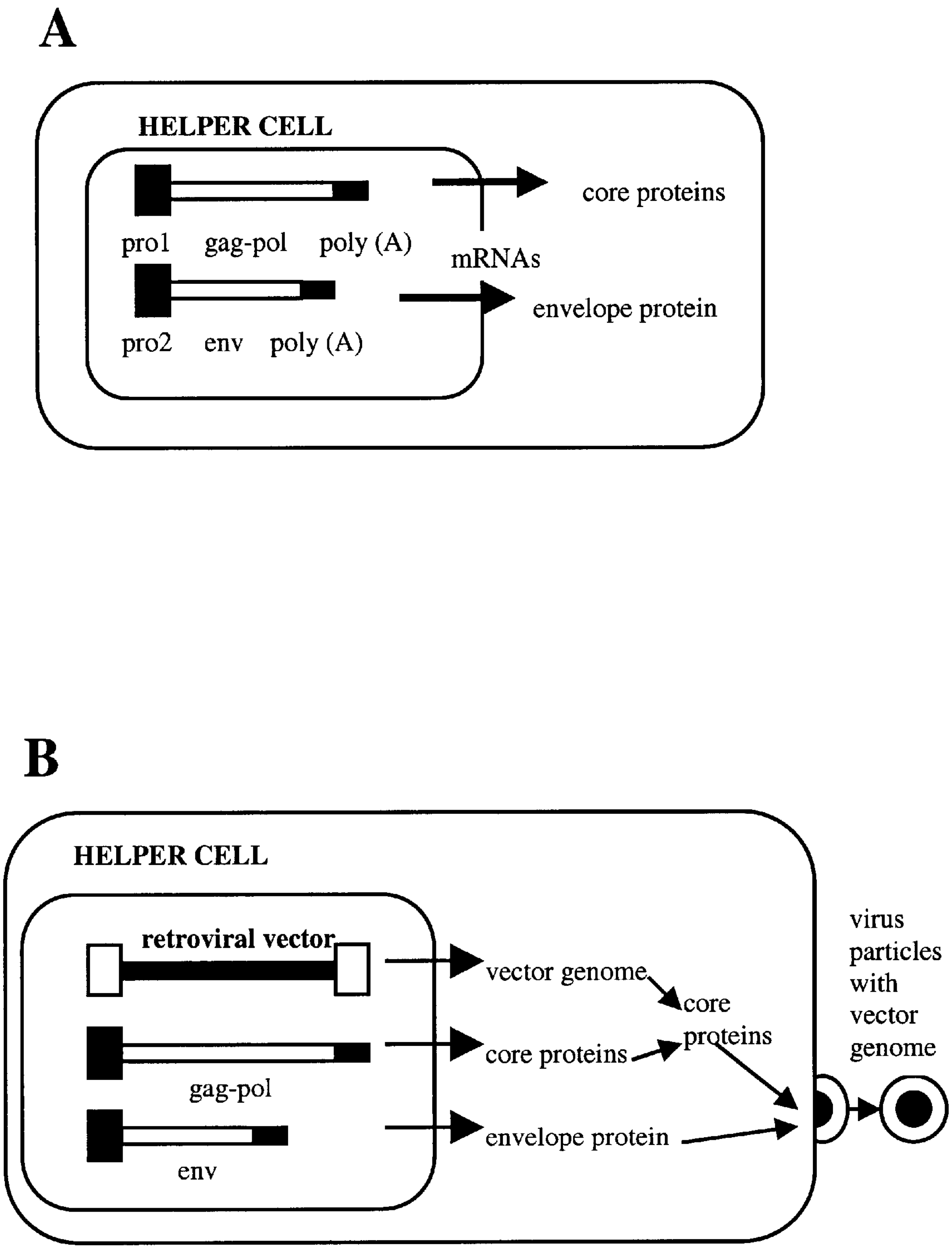
FIG. 1(parts A–B) illustrates the principle of a retroviral packaging line derived from a C-type retrovirus. (A) In helper cells retroviral proteins are expressed from different plasmid DNAs. These RNA transcripts do not contain encapsulation sequences. Thus, they are not encapsulated into retroviral particles. (B) Such helper cells are transfected with a retroviral vector plasmid construct. The RNA transcript of the retroviral vector contains an encapsulation sequence, and, therefore, is encapsulated into virions supplied by the helper cell. Supernatant tissue culture medium is used to infect fresh target cells. prol and pro2: promoters to express viral protein coding sequences; poly(A) polyadenylation sequence.

Modern helper cells contain separate plasmid constructs, which express all retroviral proteins necessary for replication (FIG. 1). After transfection of the vector genome into such helper cells, the vector genome is encapsulated into virus particles (due to the presence of specific encapsulation sequences). Virus particles are released from the helper cell carrying a genome containing only the gene(s) of interest (FIG. 1). Thus, once established, retrovirus helper cells produce gene transfer particles for very long time periods (e.g., several years). In the last decade, several retroviral vector systems have also been derived from other C-type retroviruses (Dornburg, R., *Gene Ther*., 2:301–310, 1995.; Gunzburg, W. H. and Salmons, B., *Journal of Molecular Medicine*, 74:171–182, 1996; Miller, A. D, *Hum. Gene. Ther*., 1:5–14, 1990.). However, all current retroviral vectors derived from C-type retroviruses cannot transduce genes into non-dividing cells. They only establish an infection when the target cell undergoes at least one cell division, during which the nuclear membrane is temporarily dissolved, thereby giving the virus core access to the DNA of the infected cell. (Lewis, P. and M. Emerman. *J. Virol*., 68:510–516, 1994).

To bypass this problem, efforts are underway in many laboratories to develop retroviral vectors from lentiviruses, e.g., HIV-1 or the simian immunodeficiency virus, SIV, which are able to establish a provirus in non-dividing cells. (Naldini, L, et al. 1996. *Science*, 272:263–267, 1996.) However, the fact that lentiviruses contain several regulatory proteins, which are essential for virus replication, makes the construction of lentiviral packaging cells more complicated. Furthermore, the fact that the lentiviral envelope proteins (e.g., that of HIV-1) cause syncytia and/or that some viral regulatory proteins are toxic to the cells, further hampers the development of stable packaging lines (Baltimore, D. *Cell* 82:175–176, 1995; Miller, R. H. and Sarver, N., *Mol. Med*. 1:479–485, 1995). Moreover, there are serious safety concerns regarding the use of vectors derived from highly pathogenic (deadly) retroviruses. For example, it is known that retroviruses recombine with very high efficiencies and plasmid DNAs recombine with each other very efficiently immediately after transfection. Thus, there is a concern as to whether replication-competent, pathogenic viruses arise by recombination, with the subsequent potential to cause disease in gene transduced patients (Dornburg, R., *Biol. Chem*., 378:457–468, 1997).

Many laboratories have investigated the mechanisms by which lentiviruses infect non-dividing cells. Although there is still some controversy regarding this mechanism, it known that some lentiviruses (e.g., HIV-1) contain a nuclear translocation sequence in their matrix (MA) protein, which is one of several core proteins. (Bukrinsky, M. I., et al., *Nature*, 365:666–670, 1993; Lewis, P. and Emerman, M., *J. Virol*., 68:510–516, 1994; Schwedler, U., et al., *Proc. Nati. Acad. Sci. USA*, 91:6992–6996, 1999.) Consensus nuclear translocation sequences have been identified in various proteins, which are located in the nucleus of eucaryotic cells. Such sequences are not 100% conserved, but are generally rich in the amino acids lysine, and arginine (see also FIG. 2). It has been shown that the addition (insertion) of such sequences into various proteins enabled the transport of the modified proteins, which would normally reside in the cytoplasm, into the nucleus.

C-type retroviruses such as SNV do not contain a known nuclear translocation sequence. The present invention introduces a nuclear translocation sequence into the SNV core protein, which enabled the virus particle to penetrate the nucleus of quiescent cells. The present invention relates to a system by which therapeutic genes are transduced into quiescent cells, thereby allowing for a more efficacious treatment of genetic aberrations.

Materials and Methods

Nomenclature:

Plasmid constructs are indicated by the letter p (e.g., pRD136) to distinguish them from the virus derived from the plasmid construct (e.g. RD136).

Plasmids.

The plasmid pCXL (Mikawa, T., et al., *Exp. Cell Res*., 195:516–523, 1992). contains a SNV-derived retroviral vector expressing the bacterial β-galactosidase (LacZ) gene (FIG. 3). Plasmid pIM29 contains the complete wild-type envelope gene of SNV and has been described previously (Martinez, I. and Dornburg, R., *Virology*, 208:234–241, 1995). pRD136 is a gene expression vector, which contains the complete wild-type gag and pol genes of SNV 51. Plasmid pTC53-7A5zeo is a gene expression vector derived from pTC53 33. It contains the zeocin gene, which mediates mammalian cell resistance to the antibiotic zeocin and expresses a chimeric single chain antibody (scA)—SNV envelope fusion protein (FIG. 3) to display antibody domains on the viral surface (Engelstädter T-cells by retroviral vectors displaying antibody domains selected from a phage display library, 1999 (submitted for publication). The 7A5 scA has been selected from a phage display library and has been shown to bind to an antigen expressed on human T-lymphocytes and some other hematopoietic cell types (Engelstädter, M., et al. *Targeting human T-cells by retroviral vectors displaying antibody domains selected from a phage display library*, 1999 (submitted for publication).

Site-directed Mutagenesis.

The SNV MA mutants were constructed by polymerase chain reaction (PCR) mediated site-directed mutagenesis as described (Urban, A., et al., Nucleic Acids Res., 25:2227–2228, 1997.;Picard, V., et al., *Nucleic Acids Res*., 22:2587–2591, 1994.). Briefly, a 300 bp Eag1-Stu1 fragment from pRD136, which encodes the amino terminus of the SNV-MA protein, was cloned into the vector p-Alter vector purchased from Promega. The Eag1 and Stu1 sites restriction enzyme sites were introduced in the outer PCR primers and were used for cloning the mutated DNA back into the pRD136 backbone digested with Eag1 plus Stu1. The internal primers were designed to generate mutations as indicated (FIG. 2). After this back-cloning into pRD136, the plasmid DNAs were sequenced to verify the insertion of the correct mutation. After the introduction of the first mutation, the constructs containing single mutations were used as a template to create additional mutations.

Cells

D17 cells (a dog osteosarcoma cell-ine) and the human cell lines 293T and HeLa (human cervical carcinoma) were obtained from the American Type Culture Collection ATCC, and were cultured in Dulbecco's modified Eagle's medium supplemented with 6% calf serum. The human T-lymphoid cell lines Jurkat, C8166, and H9 were obtained from the courtesy of AIDS Reagent and Repository Program, National Institute of Allergy and Infectious Diseases (Bethesda). These cells were maintained in RPMI-1640 medium containing 10% fetal bovine serum, penicillin 100 U/ml, streptomycin 100 mg/ml and 2 mM L-glutamate.

Primary Cells

Monocytes were obtained from the blood of a healthy human donor by centrifugation over Ficoll-Hypaque as described (Collman, R., et al., J. *Exp. Med*., 170:1149–1163, 1989). To obtain monocyte-derived macrophages (MDM), the monocytes were cultured at a cell concentration of $1\times10^6$/ml in modified Dulbecco's medium (MDM) supplemented with penicillin (100 U/ml), streptomycin 100 mg/mnl and 10% pooled human serum at 37° C. and 5 % $C_2$. Allowing the cells to adhere to the plastic surface without disturbance, monocytes differentiate into macrophages, which no longer undergo cell division (Collman, R., et al., *J. Exp. Med.*, 170:1149–1163, 1989). After three weeks in tissue culture, the adherent macrophages were washed with medium to free them from remaining lymphocytes.

Packaging Cell Lines

All packaging cell lines were derived from D17 cells. Following transfection protocols described previously (Martinez, I. and Dornburg, R., *Virology*, 208:234–241, 1995), a stable cell line was established, which contained the retroviral vector pCXL and the SNV-envelope gene expression vector pIM29 (Martinez, I. and Dornburg, R., *Virology*, 208:234–241, 1995). This cell line, termed DSE29B-cxl (see also FIG. 4) was used for all transient transfection/infection experiments.

Transfections and Infections

The protocol is similar to that described recently to test mutant envelope proteins (Martinez, I. and R. Dornburg, *J. Virol.*, 70:6036–6043, 1996). Briefly, a stable cell line (derived from dog D17 cells) has been established which expresses the SNV envelope protein from plasmid pIM29 (Martinez, I. and Dornburg, R., *Virology*, 208:234–241, 1995) and the retroviral vector pCXL, which transduces the bacterial β-galactosidase gene. (Mikawa, T., et al. *Exp. Cell Res.*, 195:516–523, 1992). (Chu, T. -H. and R. Dornburg, *J. Virol.*, 69:2659–2663, 1995; Chu, T. -H. and R. Dornburg, *J. Virol.* 71:720–725, 1997; Jiang, A., et al., *J. Virol.*, 72:10148–10156, 1998; Martinez, I. and R. Dornburg, Virology, 208:234–241, 1995). Using the lipofectamine transfection protocol (supplied by Gibco) and following the procedure recommended by the supplier, plasmids expressing wild-type Gag-Pol or constructs expressing Gag-Pol containing mutations in MA were transfected into DSE29B—cxl cells. 48 hours after transfection virus was harvested from confluent cultures and normal dividing as well as growth-arrested D17 cells were infected.

Transient transfections were performed using the lipofectamine purchased from Bethesda Research Laboratories following the protocol recommended by the supplier. Briefly, for each transfection, $6\times10^5$ DSE29B-cxl cells were plated on a 60 mm diameter plastic dishes the day before transfection; 10 μg DNA was mixed in 15 μl lipofectamine. The cells were incubated with the DNA-lipofectamine mixture in 500 μl serum-free medium for 5 hrs. After the removal of this mixture form the cells, 3 ml of fresh medium was added and the cell free supernatant was used for infection studies 48 hrs after transfection as described (Chu, T.-H. and Dornburg, R., *J. Virol*, 69:2659–2663, 1995). Infections of D17 cells were performed as described previously (Chu, T.-H., et al., *Gene. Ther.*, 1:292–299, 1994; Chu, T.-H. and Dornburg, R., *J. Virol.*, 71:720–725, 1997; Jiang, A., et al, *J. Virol.*, 72:10148–10156, 1998). Human macrophages and T-cells were infected with vector virus for 5 hours in the presence of polybrene (10 μg/ml). To determine the number of cells expressing the bacterial LacZ gene, infected cells were stained with 5 bromo-4-chloro-3-indolyl-b-D-galactopyranoside (X-gal) 48 hours after infection as described elsewhere (Mikawa, T., et al., *Exp. Cell Res.*, 195:516–523, 1992).

Growth Arrest of Cells

Cells were growth-arrested with either mitomycin (D17 cells: 2 μg/ml; human cells: 1 g/ml), aphidicolin (5 μg/ml), mimocin (400 μM), or hydroxyurea (2.5 mM) as described 15,43. Briefly, D17 cells or human T-cell-lines were first synchronized in serum-free medium overnight before the addition of these chemicals. After infection with retroviral vectors, the cells were washed and cultivated in fresh medium containing the inhibitor of mitosis for 48 hours before X-gal staining. Gamma radiation: D17 cells were cultured in serum free medium overnight before irradiation using 4000 rads.

FACS Analysis of Growth Arrested Cells

Aliquots of $1\times10^4$ cells were fixed in 70% ethanol for 15 minutes followed by RNAase treatment (180 μg/ml) for 30 mins at RT. Next the DNA was stained with propidium iodide (50 μg/ml) at room temperature for 1 hr. Cells were evaluated by Fluorescence-activated cell sorter (FACS) analysis and the percentage of total viable cells in G1, S, and G2/M phases of the cell-cycle was calculated by using the Cell-Fit software (Becton Dickinson).

Experimental System

To test, whether the introduction of a nuclear translocation sequence into the core protein of a retrovirus would enable the virus to infect quiescent cells, the following considerations were made:

1. The modification of the core protein should not dramatically impair protein folding, as an aberrantly folded protein may lead to impairment of virus core particle formation and/or function.

2. The nuclear translocation sequence should be at a similar position as that of a lentivirus, e.g., HIV-1, which is located in the MA protein. In nature, many proteins of different species, which fulfill similar functions are folded in a very similar way, although their amino acid sequences can be considerably different. Thus, the MA proteins of HIV-1 and SNV are folded in a similar way. Furthermore, the introduction of a nuclear translocation sequence into MA of SNV at a position homologous to that of HIV-1 has the highest probability that the resulting genetically modified protein will function similarly to that of HIV-1.

Comparison of the amino acid sequences of HIV-1 and spleen necrosis virus, SNV, an avian C-type reticuloendotheliosis virus, revealed that the MA sequence of SNV was similar to that of HIV-1 in the region which contains the consensus HIV-1 translocation sequence (FIG. 2). Two out of the 7 amino acids which form the nuclear translocation sequence in HIV-1 were identical in SNV. At another position, SNV contained an arginine rather than a lysine, as in HIV-1. However, judging from different HIV-1 translocation sequences, the amino acids lysine and arginine, both basic and structurally similar amino acids, are interchangeable without impairing biological function. Thus, site-directed mutagenesis was used to convert the SNV sequence into an HIV-1 consensus nuclear translocation sequence in this particular region (FIG. 2). A determination was made regarding whether each individual or combination of mutations would interfere with virus replication and whether such mutations would endow the virus with the ability to infect quiescent cells. In these experiments a transient transfection/infection assay was used (FIG. 4).

Infectivity in Dividing and Growth-arrested D17 Cells

None of the mutations introduced into MA of SNV impaired retroviral replication. This conclusion is based on the finding that D17 cells were infected at comparable levels by particles containing wild-type or mutant MA proteins. The supernatant medium of DSE29B cells transiently transfected with the Gag-Pol constructs, without the targeting Env-plasmid, was used to infect dividing D17 tissue culture cells. Virus harvested from cells transfected with the wild-type Gag-Pol expression vector pRD136 transduced the lacZ marker gene into D17 cells with titers of $1\times10^3$ cfu/ml (Table 1). This titer is approximately 1,000 fold lower than that obtained using a similar stabile transfected helper cell-line, e.g., DSH-cxl cells (Dornburg, R., *Gene Ther*., 2:301–310, 1995, Jiang, A., et al., *J. Virol*., 72:10148 –10156, 1998), and is comparable to titers obtained in other previous transient transfection/infection experiments (Chu, T.-H. and Dornburg, R., *J. Virol*., 69:2659–2663, 1995), using the components of the SNV vector system described in the present invention. All mutants transduced the lacZ vector with an efficiency very similar to that of wt-Gag-Pol (Table 1). One mutant (RD136-m7), which contained two point mutations towards a complete HIV-1 consensus nuclear translocation signal sequence (FIG. 2), gave consistently two-fold higher virus titers than all other constructs (Table 1).

To get a first insight into whether the mutation(s) introduced in MA were sufficient for the virus core to penetrate the nucleus of non-dividing cells, the infectivity of all particles was determined on D17 cells, growth-arrested with mitomycin, which blocks the cell-cycle in the G1 phase of mitosis (Lewis, P. and Emerman, M., *J. Virol*., 68:510–516, 1994; Stevenson M. and Gendelman, H. E., *J. Leukoc. Biol*., 56:278–288, 1994; Huang, Z. B., et al., *J. Virol*., 67:6893–6896, 1993). Growth arrest of D17 cells was verified by FACS analysis as described (Lewis, P. and Emerman, M., *J. Virol*., 68:510–516, 1994; Stevenson M. and Gendelman, H. E., *J. Leukoc. Biol*., 56:278–288, 1994; Huang, Z. B., et al., *J. Virol*., 67:6893–6896, 1993). These FACS analyses indicated that more than 90% of the cells were arrested in the G1 phase of the cell-cycle (FIG. 5). Particles containing wild-type MA or a mutant MA with one point mutation were not able to establish a provirus in growth-arrested D17 cells (Table 1). These data verify that wild-type SNV, like all other C-type retroviruses investigated, is not able to infect quiescent cells. However, four MA variants containing a complete, or nearly complete, HIV-1 nuclear translocation signal sequence were able to infect growth-arrested cells. Surprisingly, RD136-m7, a mutant containing only 4 out of 6 amino acids identical to the HIV-1 consensus nuclear translocation signal sequence, (SEQ. ID NO: 11) gave the highest gene transfer efficiency into growth-arrested cells and consistently transduced the lacZ marker gene almost two-fold better than a mutant containing the complete HIV-1 nuclear translocation signal sequence (RD136-m8, FIG. 2 and Table 1). Overall, titers in growth-arrested cells were only two-fold lower than those obtained in dividing cells (Table 1).

To further test and verify infectivity of the MA mutants in growth-arrested cells, a series of experiments was performed using gamma irradiated or non-irradiated D17 cells, which were arrested with four different inhibitors of mitosis (Table 2). Gamma irradiation blocks mitosis at the S/G2 phase (Bukrinsky, M. I., et al., *Nature*, 365:666–670, 1993; Lewis, P. and Emerman, M., *J. Virol*., 68:510) –516, 1994; Schwedler, U., et al., *Proc. Natl. Acad. Sci. USA*, 91:6992–6992, 1999; Miyake, K., et al., *Hum. Gene Ther*., 9:467–475, 1999). Aphidicolin, mitomycin, mimocin and hydroxyurea, arrest cells in the G1/S phase. The transfection/infection protocol was identical to that described above. FACS analysis performed with aliquots of all growth-arrested cells immediately before infection confirmed that more than 98% of the cells were growth-arrested. Virus particles containing the wild-type SNV-MA protein could not infect any of the growth-arrested D17 cells (Table 2). However, all mutants, which were able to infect mitomycin-arrested D17 cells were also able to infect non-radiated, as well as radiated, D17 cells with similar titers, regardless of which inhibitor of mitosis was used. Again, RD136-m7 revealed the highest gene transfer efficiency (Table 2).

In summary, neither virus particles containing wild-type MA nor particles containing a single point mutation were able to infect growth-arrested D17 cells. Only particles which contained an MA protein in which a complete nuclear translocation sequence has been inserted were able to efficiently infect growth-arrested (quiescent) D17 cells. These data show that the introduction of a nuclear translocation signal sequence into the core protein of SNV was sufficient for the SNV viral pre-integration complex to actively enter the nucleus of quiescent cells. One MA mutant, RD136-m7, gave consistently the highest virus titers. Thus, it was selected to perform further infectivity studies in human cells.

Infectivity in Human Cells

SNV vector particles with wt-SNV envelope proteins are not infectious in human cells (Dornburg, R., *Gene Ther*., 2:301–310, 1995); Chu, T.-H. and Dornburg, R. *J. Virol*., 69:2659–2663, 1995; Jiang, A., et al., *J. Virol*., 72:10148) –10156, 1998; Blaese, R. M., et al., Science, 270:475–480, 1995). However, a highly efficient, cell-type-specific gene transfer into human cells can be obtained, when a targeting envelope is co-present with wild-type Env (Chu, T.-H. and Dornburg, R., *J. Virol*., 69:2659–2663, 1995; Chu, T.-H., et al., *Gene Ther*., I:292–299, 1994; Chu, T.-H. and Dornburg, R., *J. Virol*., 71: 720–725, 1997; Jiang, A., et al., *J. Virol*., 72, 10148–10156, 1998; Engelstädter, M., et al. *Targeting human T-cells by retroviral vectors displaying antibody domains selected from a phage display library*, 1999 (submitted for publication)). Thus, to test infectivity in dividing and non-dividing human. cells, transfection into DSE29B-cxl cells was performed with the Gag-Pol expression vectors plus a plasmid expressing the scA-Env chimeric fusion protein (pTC53-7A5-zeo, FIGS. 3 and 4). The scA recognizes an antigen present on human T-lymphocytes and other hematopoietic cells. As a result, the packaging lines produce vector particles with two envelopes capable of infecting human T-lymphocytes with high efficiency (Engelstädter, M., et al. *Targeting human T-cells by retroviral vectors displaying antibody domains selected from a phage display library*, 1999 (submitted for publication)). All transfection/infection protocols were performed as described above. Infectivity was tested in the human T-lymphocyte cell lines C8166, Jurkat, and H9. Cell-division was blocked with mitomycin and cells were analyzed by FACS analysis as described above (for an example, see FIG. 5).

Virus particles containing the wt-MA protein and targeting envelopes were able to infect all dividing T-cell-lines with titers up to $5 \times 10^2$ (Table 3). In a similar way, mutant RD136-m7 infected such human cells with an efficiency similar to, or slightly higher than, that of SNV with wt-Gag-Pol (Table 3). Of note, a vector virus titer of $5 \times 10^2$ was approximately 4,000-fold lower than that obtained with a stable packaging cell-ine, which expressed the lacZ vector and the wild-type viral particle proteins from the same gene expression plasmids. (Engelstädter, M., et al. *Targeting human T-cells by retroviral vectors displaying antibody domains selected from a phage display library*, 1999 (submitted for publication). This much lower titer reflects the transient double-transfection protocol, in which only a small percentage of the transfected helper cells express relatively low amounts of all viral proteins necessary for complete virus particle assembly. Virus particles containing the wild-type MA and targeting Env were not able to infect any of the T-cell-lines which were growth-arrested with mitomycin. However, RD136-m7 was able to significantly infect such growth-arrested cells (Table 3). These data confirm the results obtained in dog D17 cells and show that the nuclear translocation signal sequences in the SNV-MA is sufficient to allow infection of growth-arrested human cells. To test this further, a stable cell-line was created, which continuously expresses all retroviral particle proteins. Briefly, DSE29B-cxl cells were transfected with pRD136-m7 in co-transfection with plasmid pTC53–7A5zeo, followed by zeocin selection. Five individual zeocin resistant colonies were isolated and cell-lines were established from such clones. All clones were briefly tested for their ability to transduce the lacZ gene into dividing human T-lymphocytes and the clone with the highest gene transduction efficiency was selected for further experiments. Virus was harvested from confluent tissue culture plates and infectivity experiments were performed with dividing and growth-arrested human T-lymphocytes, as described above. T-lymphocytes were infected with serial virus dilutions and the number of lacZ-transduced cells was determined. Dividing C8166 cells were infected with a titer of $6\times10^5$ cfu/ml. Titers in growth-arrested C8166 cells was $3\times10^5$ cfu/ml (Table 3). Similar results were obtained in growth-arrested H9 cells (Table 3). These data confirm that the mutation introduced in MA enables the high-efficiency infection of non-dividing cells.

Proviruses in the Nucleus

To further investigate whether the vector DNA had entered the nucleus, infection experiments (including FACS analysis before infection and before isolating the DNA as described above, FIG. 6A) were repeated with growth arrested D17 cells, H9 cells, and Jurkat cells. DNA was isolated from purified nuclei of dividing and non-dividing cells infected with vector particles containing wt-MA or the m7-MA. The DNA was analyzed for the presence of viral proviruses by PCR technology with primers specific for the lacZ gene, which is only present in the vector DNA. To verify that the amplified DNA represented a fragment of the lacZ gene, the PCR products were blotted on a nitrocellulose filter and hybridized with a radioactive-labelled lacZ DNA (FIG. 6). In addition, infectivity was verified in parallel experiments by lacZ staining of aliquots of infected cells at the time chromosomal DNA was extracted and another aliquot one week after chromosomal DNA extraction (FIG. 6A). FACS analysis confirmed the growth-arrest (FIG. 5) and lacZ staining confirmed infectivity of growth-arrested cells by RD136-m7, but not with pRD136 wild-type MA. PCR amplification with primers specific for the lacZ gene were expected to amplify a 352 bp fragment. In control experiments, DNA isolated from nuclei of DSE29B-cxl cells and DNA from infected cells were also subjected to PCR. DSE29B-cxl cells contain transfected copies of the retroviral vector pCXL. PCR amplification of this control DNA resulted in a DNA band which migrated in an agarose gel at the expected size. An additional smaller band was also seen, which was the result of a non-specific PCR amplification (FIG. 6). No DNA bands were seen in control experiments with DNA isolated from the nuclei of uninfected D17 cells or 119 cells (FIG. 6). These data show that the PCR-amplified fragment was specific for the lacz gene. Bands specific for the lacZ gene were obtained from DNAs isolated from nuclei of dividing cells infected with wild-type vectors (FIG. 6). However, no, or very little, lacZ PCR products were obtained from DNAs of growth-arrested H9 or D17 cells, respectively, infected with wild-type vectors. In contrast, lacZ specific DNA was obtained from DNA of growth arrested D17, H9, or Jurkat cells infected with vectors containing an nuclear translocation signal sequence. These data confirm that the cores of vector particles containing a nuclear translocation signal sequence were imported into the nucleus of non-dividing cells. However, these data cannot distinguish between integrated and non-integrated vector DNA. Thus, another aliquot of the cells has been kept in tissue culture for another week without the inhibitor of mitosis to let the cells undergo cell divisions. The cells were then stained with X-gal to test for lacZ expression. The virus titer of infected cells had not decreased and blue cell colonies derived from single infected cells indicated that the provirus had indeed integrated into the genome.

Infection of Quiescent Primary Macrophages

Figure 7A:
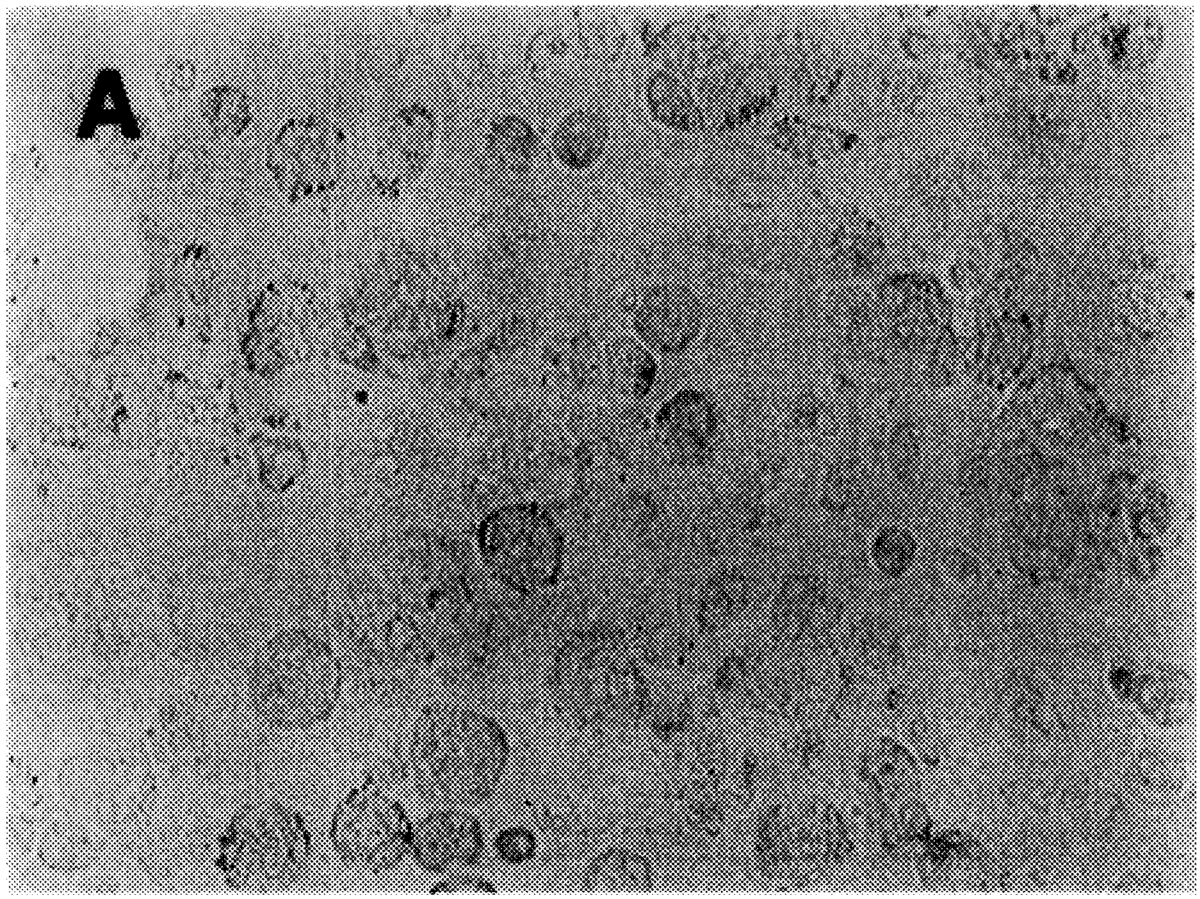
Figure 7B:
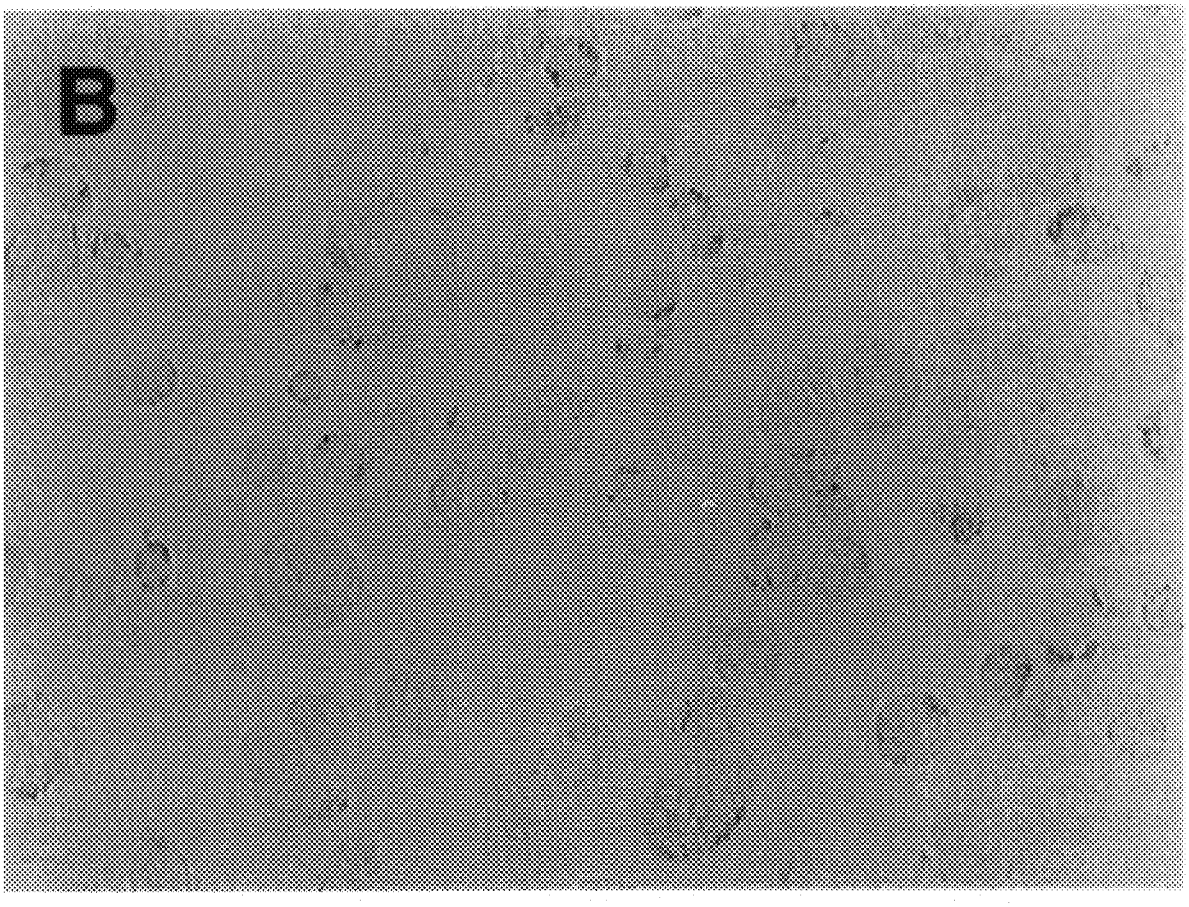
Figure 7C:
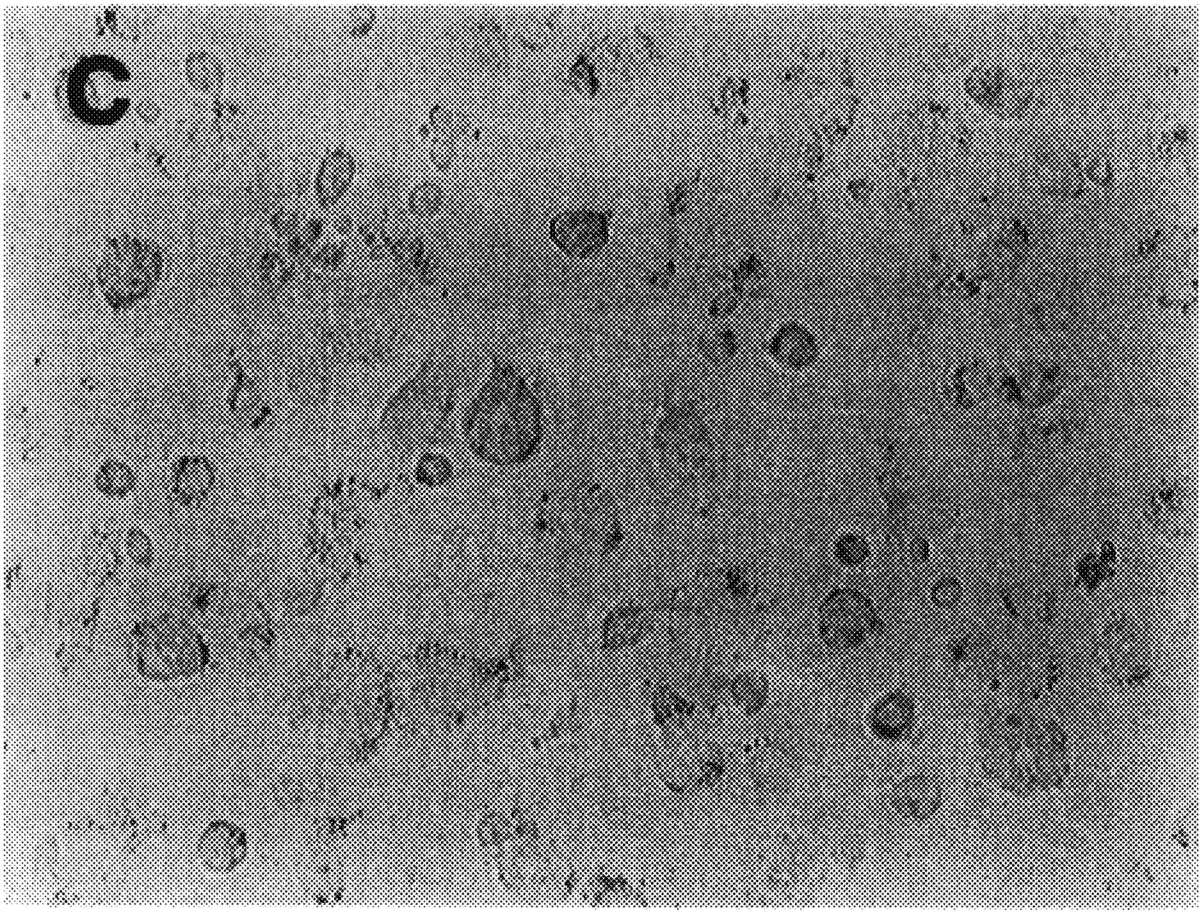
Figure 7D:
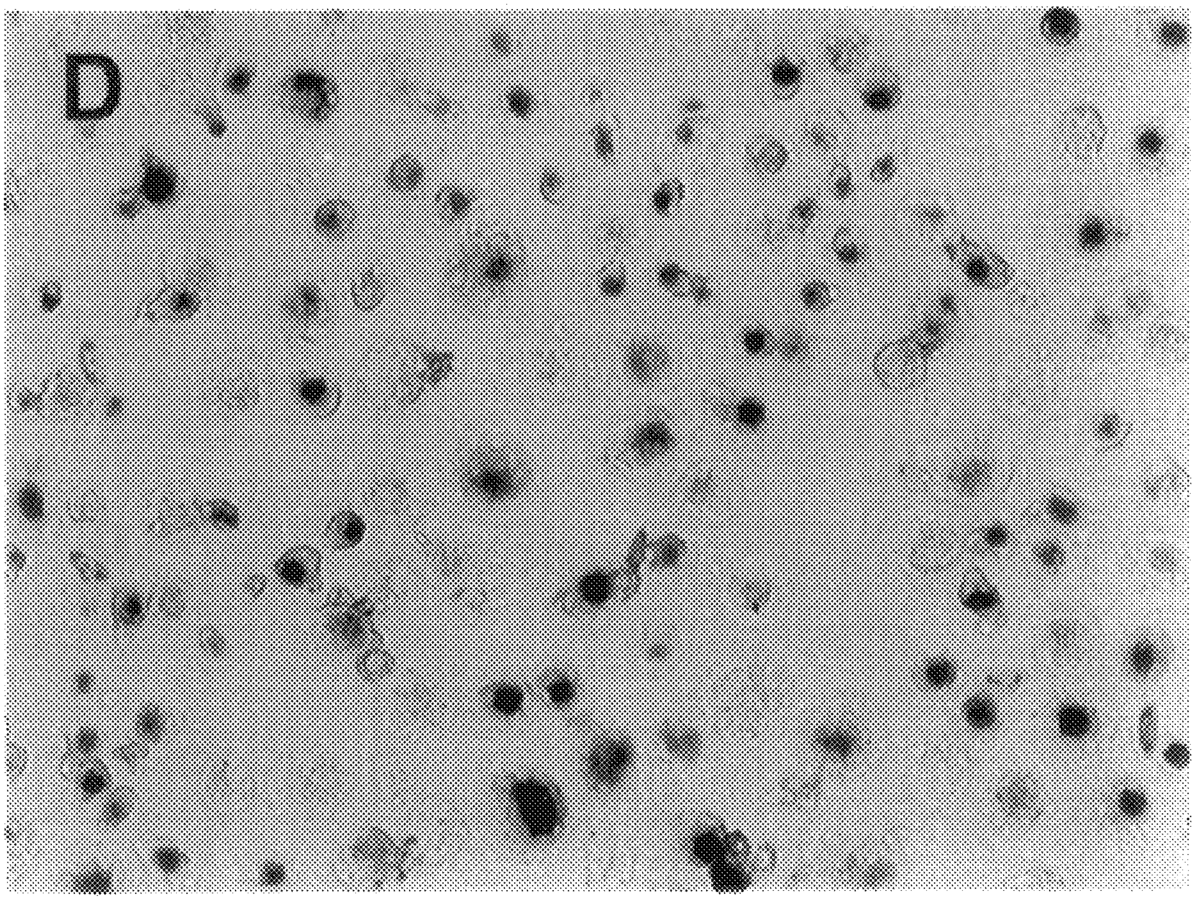

The ultimate tests to determine the ability of a vector to infect non-dividing cells, are infectivity experiments using truly quiescent cells. Human primary monocyte-derived macrophages can be kept in tissue culture for several weeks, although such cells do not further divide at this stage. They are considered completely quiescent (Huang, Z. B., et al., *J. Virol.*, 67:6893–6896, 1993; von Schwedler, U. et al., *Proc. Nati. Sci. USA*, 91:6992–6996, 1994; Collman, R., et al. *J. Exp. Med.*, 170:1149–1163, 1989). To obtain monocyte-derived macrophages (MDM), blood-derived monocytes were allowed to adhere to the plastic surface of tissue culture dishes without disturbance and cultivated for three weeks. After this time period, aliquots of the cells were subjected to FACS analysis. This analysis confirmed the complete quiescent state of such cells. The rest of the cells were infected with vector virus harvested from four different packaging lines. As expected, vector virus particles containing wt-MA and wt-Env only, did not infect quiescent macrophages at all (FIG. 7A). No infectivity (virus titers<1) was observed with virus particles containing wt-MA, wt-Env plus targeting Env or with particles containing the RD136-m7-derived MA and wild-type Env only (FIGS. 7B and 7C). The latter particles are unable to penetrate the target cell. However, up to 90% of the quiescent macrophages (titer $1.2\times10^5$ cfu/ml) were infected by particles, which contained the RD136-m7-derived MA protein and displayed wt-Env plus targeting Env (FIG. 7D). These data indicate that a nuclear translocation signal sequence in the MA protein of SNV enables the virus to actively penetrate the nucleus of non-dividing cells and to express transgenes.

Discussion

All wild-type C-type retroviruses investigated have been found not to be able to infect quiescent cells. Thus, the use of retroviral vectors derived from C-type viruses, such as MLV, for human gene therapy is very limited (Lewis, P. and Emerman, M., *J. Virol.*, 68:510–516, 1994). Lentiviruses such as HIV-1 or simian immunodeficiency virus (SIV-1) are able to infect quiescent cells. Although the mechanism of nuclear penetration by HIV-1 is not fully understood, it is known that HIV-1 contains a nuclear localization sequence, (SEQ. ID. NO: 11) which is located in the amino terminal part of the MA protein. It has been suggested that it triggers the nuclear import of the HIV-1 pre-integration complex (Bukrinsky, M. I., et al., *Nature*, 365:666–670, 1993; Lewis, P. & Emerman, M., *J. Viriol.*, 68:510–516, 1994; Schwedler, U., et al., *Proc. Natl. Acad. Sci. USA*, 91: 6992–6996, 1999; Miyake, K., et al., *Hum. Gene Ther.* 9:467–475, 1999) (FIGS. 3 and 4). No nuclear localization sequence -like sequence could be identified in the MA of wt-SNV.

The introduction of a nuclear localization sequence into the MA protein of SNV is sufficient to trigger the active import of the SNV pre-integration complex into the nucleus of an infected cell. Introducing the nuclear localization sequence in the SNV-MA protein at a position homologous to that in HIV-1 will have the highest chance of success for the following reason: it is widely accepted that all retroviruses evolved from a common ancestor millions of years ago (Temin, H. M., *J. Natl. Cancer Inst.*, 46:3–7, 1971; Coffin, J. M., *Curr. Top. Microbiol. Immunol.*, 176:143–164, 1992). Thus, although the amino acid sequences of homologous retroviral proteins differ considerably in different retroviruses, all retroviruses still share the same overall mechanisms of replication. During evolution, the structural proteins of different retroviruses acquired different mutations. However, although considerably different in sequence, such proteins may still fold in a very similar way to fulfill their biological function, as in the case of many cellular proteins (e.g., hemoglobin). Thus, the MA protein of SNV and HIV-1, although considerably different in amino acid sequence, still fold in a similar way. Thus, introducing the nuclear translocation signal sequence at a position similar to that in HIV-1 would expose the introduced nuclear translocation signal sequence as an endogenous motif and, therefore, would be recognized by cellular protein complexes involved in the nuclear import of proteins or protein complexes.

To test this hypothesis, a series of different mutations were introduced into the MA protein of SNV. In the position at which the nuclear translocation signal sequence of HIV-1 (SEQ. ID. NO: 11) is located, SNV revealed a similar sequence (SEQ. ID. NO: 1). That is, two lysine residues, which are an essential part of nuclear translocation signal sequence, were already present (position 2 and 3). Moreover, at the fourth position, at which HIV-1 contains a lysine (or glutamine), SNV contained an arginine residue. Arginine seems to be exchangeable with lysine, since different HIV-1 isolates contain either arginine or lysine at the sixth position (FIG. 2). Thus, it appeared that a maximum of three amino acid exchanges were necessary to introduce a nuclear translocation signal sequence into the SNV-MA.

To test whether any of the mutations had a negative effect on viral replication, and to determine, whether the mutation (s) would endow the virus particle with the ability to actively enter the nucleus of an infected cell, a series of mutants was created and investigated individually. All mutations were tested in a transient transfection I infection assay system. The disadvantage of this assay system is that only relatively low vector virus titers can be obtained. A titer of $10^3$ cfu/ml appears to be the upper limit using the plasmids described and dog D17 cells (30,32,34). However, the main advantage of this system is that virus titers represent a statistically significant average virus titer produced from thousands of transfected cells. Moreover, the spontaneous production of replication-competent virus has never been observed using the components of this vector system (Martinez, I. and Dornburg, R., *Hum. Gene Ther.*, 7:705–712, 1996). This allowed the direct comparison of the biological activity of the different constructs.

Using this experimental system, wild-type SNV was completely unable to infect quiescent cells. Moreover, the introduction of a single mutation, which had no effect on normal viral replication, was also not sufficient to enable the infection of quiescent cells. However, the introduction of at least two mutations endowed the MA protein with a viable nuclear translocation signal sequence. Surprisingly, one mutant, RD136-m7, which contained only two substitutions at amino acid positions 5 and 6 (28 and 29 in the AA sequence), consistently revealed the highest infectivity in all experiments, and gave slightly higher vector virus titers than a mutant containing the complete HIV-1 consensus nuclear translocation signal sequence (SEQ. ID. NO: 11). Even further, the efficiency of infection in dividing cells of this double mutant was reproducible higher than that of wt-SNV. The slight increase in titer may reflect that viral pre-integration complexes containing this mutant MA did not have to remain in the cytoplasm until the nuclear membrane dissolves and, therefore, had a lower chance of being degraded by cellular proteases or nucleases during a "waiting period" imposed on wt-SNV.

Viral titers of a few hundred to one thousand cfu/ml appear to be low in comparison to titers obtained from comparable stable packaging lines ($10^6$ cfu/ml), which had been selected from a single high producer clone (Engelst ädter, M., et al., *Targeting human T-cells by retroviral vectors displaying antibody domains selected from a phage display library*, 1999 (submitted for publication)). However, reproducible virus titers ranging between 100 to 1,000 cfu/ml are still high enough to allow conclusions, in particular, because the background infectivity of control constructs consistently remained at undetectable levels (<1 cfu/ml). Overall, virus titers in growth-arrested cells were slightly lower than that obtained in dividing cells. However, this decrease in titer also reflects the biological condition of growth-arrested cells, since many cells undergo apoptosis, i.e: programmed cell death, during the growth-arrest imposed by the inhibitors of mitosis, a very well known observation (Bukrinsky, M. I., et al., *Nature*, 365:666–670, 1993; Lewis, P. and Emerman, M., *J. Virol.*, 68:510–516, 1994; Schwedler, U., et al., *Proc. Natl. Acad. Sci. USA*, 91:6992–6996, 1999; Miyake, K., et al., *Hum. Gene Ther.*, 9:467–475, 1999; Stevenson, M. and Gendelman, H. E., *J. Leukoc. Biol.*, 56:278–288, 1994). However, the virus titers observed (up to 500 over a background of no

TABLE 1

VIRUS TITERS OF SNV-GAG MUTANTS ON D17 CELLS

| | aa-sequence | virus titer (cfulml) dividing cells | growth-arrested cells |
|---|---|---|---|
| SNV y | phe-**lys-lys**-*arg*-ala-gly (wild-type) | 1 × $10^3$ | <1 |
| RD136-m1 | **gly-lys-lys**-*arg*-ala-gly | 1 × $10^3$ | <1 |
| RD136-m2 | phe-**lys-lys-lys**-ala-gly | 1 × $10^3$ | <1 |
| RD136-m3 | phe-**lys-lys**-*arg*-**tyr**-gly | 1 × $10^3$ | <1 |
| RD136-m4 | phe-**lys-lys**-*arg*-ala-**lys** | 1 × $10^3$ | <1 |
| RD136-m5 | **gly-lys-lys**-*arg*-**tyr**-gly | 1 × $10^3$ | 1.5 × $10^2$ |
| RD136-m5b | **gly-lys-lys-lys-tyr**-gly | 1 × $10^3$ | 1.5 × $10^2$ |
| RD136-m6 | **gly-lys-lys**-*arg*-ala-**lys** | 1 × $10^3$ | 1.5 × $10^2$ |

TABLE 1-continued

VIRUS TITERS OF SNV-GAG MUTANTS ON D17 CELLS

| | aa-sequence | virus titer (cfulml) dividing cells | virus titer (cfulml) growth-arrested cells |
|---|---|---|---|
| RD136-m7 | phe-lys-lys-*arg*-tyr-lys | $2 \times 10^3$ | $5 \times 10^2$ |
| RD136-m8 | gly-lys-lys-lys-tyr-lys | $1 \times 10^3$ | $3.3 \times 10^2$ |

Table 1: Virus particles were harvested from DSE29B-xcl cells transfected with plasmids encoding SNV gag-pol proteins (wt or mutant) and dividing or growth-arrested D17 cells were infected. Virus titers, expressed as colony forming units per ml supernatant medium (cfu/ml), were determined 48 hours after infection by counting clue cell colonies (2 or 4 adjacent cells), or in the case of growth-arrested single blue cells. The titers presented here are averaged from three independent experiments.

TABLE 2

VIRUS TITER OF SNV GAG MUTANTS IN GROWTH-ARRESTED D17 CELLS

| | aphidicolin | | mitomycin | | mimocin | | hydroxyurea | |
|---|---|---|---|---|---|---|---|---|
| | nr | r | nr | r | nr | r | nr | r |
| RD136 (wild-type) | <1 | <1 | <1 | <1 | <1 | <1 | <1 | <1 |
| RD136-m5 | $1.6 \times 10^2$ | $1.5 \times 10^2$ | $1.5 \times 10^2$ | $1.6 \times 10^2$ | $2 \times 10^2$ | $1.6 \times 10^2$ | $2 \times 10^2$ | $2.1 \times 10^2$ |
| RD136-m5b | $1.4 \times 10^2$ | $1.5 \times 10^2$ | $1.5 \times 10^2$ | $1.6 \times 10^2$ | $1.4 \times 10^2$ | $1.3 \times 10^2$ | $1.6 \times 10^2$ | $1.5 \times 10^2$ |
| RD136-m6 | $1.2 \times 10^2$ | $1.2 \times 10^2$ | $1.0 \times 10^2$ | $1.1 \times 10^2$ | $1.2 \times 10^2$ | $1.1 \times 10^2$ | $1.2 \times 10^2$ | $1.1 \times 10^2$ |
| RD136-m7 | $3.6 \times 10^2$ | $3.8 \times 10^2$ | $5.0 \times 10^2$ | $4.8 \times 10^2$ | $4.6 \times 10^2$ | $4.8 \times 10^2$ | $5.1 \times 10^2$ | $5.4 \times 10^2$ |
| RD136-m8 | $3.1 \times 10^2$ | $3.0 \times 10^2$ | $3.0 \times 10^2$ | $3.2 \times 10^2$ | $3.3 \times 10^2$ | $3.2 \times 10^2$ | $3.5 \times 10^2$ | $3.5 \times 10^2$ |

Table 2: Virus particles were harvested from DSE29B-cxl cells transfected with plasmids encoding SNV gag-pol proteins (wt or mutant) and radiated (r) or non-radiated (nr), growth-arrested D17 cells were infected. Virus titers, expressed as colony forming units per ml supernatant medium (cfu/ml), were determined 48 hours after infection by counting blue cells. The titers presented here are averaged from three independent experiments. Cells were radiated before or after the inhibitor of mitosis was averaged from no difference in virus titer was observed.

TABLE 3

INFECTIVITY OF SNV IN HUMAN T-LYMPHOCYTES (cfu/ml)

| | C8166 | | H9 | | Jurkat | |
|---|---|---|---|---|---|---|
| | dividing | growth-arrested | dividing | growth-arrested | dividing | growth-arrested |
| RD136 (wt) | $5.5 \times 10^2$ | <1 | $1.5 \times 10^2$ | <1 | $1.0 \times 10^2$ | <1 |
| RD136-m7 | $5.0 \times 10^2$ | $1.8 \times 10^2$ | $3.2 \times 10^2$ | $1.0 \times 10^2$ | $2.0 \times 10^2$ | $1.0 \times 10^2$ |
| RD136-m7 stable | $6.0 \times 10^5$ | $3.5 \times 10^5$ | $2.0 \times 10^5$ | $1.0 \times 10^5$ | nd | nd |

Table 3: Virus was harvested from DSE29B-cxl cells transiently transfected with SNV-gag-pol expression vectors plus a plasmid for the expression of a targeting envelope (RD136 (wt) and RD136m7). The targeting envelope was a chimeric scA-TM protein. The scA (termed 7A5) recognizes an antigen present on human T-lymphocytes and macrophages. Infectivity experiments were performed in the human T-cell lines indicated. Growth-arrest was induced with mitomycin. The data presented are the average of two sets of independent experiments, in which very similar results were achieved. The bottom row shows virus titers obtained from a stable packaging line (RD136-ml-stable) transfected with pRD136-m7 and pTC53–7A5zeo. nd: not done. infected cells in control experiments) clearly show that the SNV with a nuclear translocation signal sequence is able to infect non-dividing cells. In addition, initial experiments indicate that more than 1,000-fold higher virus titers can be obtained in quiescent T-lymphocytes and macrophages using vector virus harvested from a stable packaging line. Moreover, even higher titers may be obtained be screening and selecting a single high producer clone from a large number of isolated cell clones.

To further prove that vector cores containing a nuclear translocation signal sequence entered the nucleus of growth-arrested cells, PCR analysis of chromosomal DNAs isolated from nuclei of dividing and growth arrested D17 cells, H9 cells, and Jurkat cells was performed. The vector DNA was present only in the nuclei of growth-arrested cells infected with vector particles containing a nuclear translocation signal sequence. Although these data can not distinguish between integrated and non-integrated vector DNA, they clearly show that the viral pre-integration complex had entered the nucleus of quiescent cells. Unfortunately, there is no clear experimental approach to distinguish between integrated and non-integrated vector DNA in these types of experiments. However, integration of the viral DNA is mediated by the integrate (IN) protein and is independent from MA. Since no modifications have been made in other parts of the SNV vector, or sequences coding for other proteins such as IN, the vector DNA integrated into the genome. This is further supported by the finding that SNV replication and gene expression is dependent on viral DNA integration.

In summary, this is the first report which shows that a genetically engineered C-type retrovirus is capable of infecting quiescent cells. This conclusion is based on the following observations: wt-SNV or four genetic mutants were completely unable to infect quiescent cells (titers below 1 cfu/ml). However, the introduction of the nuclear translocation signal sequence enabled the virus to infect (i) growth-arrested D17 cells, radiated or non-radiated and arrested with four different inhibitors of mitosis; (ii) growth-arrested human T-lymphocytes; and (iii) quiescent human macrophages. This conclusion is further supported by DNA analysis, which shows that vector DNA is present in the nuclei of growth-arrested cells infected with RD136-m7, but not in growth-arrested cells infected with vectors containing the wt-)

MA protein. Infectivity in human cells was only observed when a targeting envelope was present in the virus particles. Thus, the present invention provides an extremely powerful vector system using SNV, since it enables cell-type-specific gene delivery into quiescent cells. This will open a significant variety of future in vivo human gene therapy applications for this non-pathogenic and safe gene transfer system.

I claim:

1. At least one retroviral vector derived from at least one spleen necrosis virus (SNV), wherein said SNV is capable of infecting non-dividing cells.

2. A method of generating retroviral vector particles, wherein at least one SNV is manipulated to obtain a retroviral vector expressing a targeting envelope protein on a surface of said particles wherein said particles are capable of cell-type specific infection by said targeting envelope protein on said surface of said particles' binding to a receptor on a target cell for cell-type specific gene transfer into non-dividing cells and wherein said retroviral vector particles further contain a SNV retroviral expression vector wherein a matrix protein has been mutated to introduce a nuclear translocation sequence at a position homologous to that in HIV-1.

3. A method of infecting quiescent cells, comprising introducing retroviral vectors, which are encapsulated in retroviral vector particles, into said quiescent cells, wherein said retroviral vectors comprise at least one SNV retroviral vector, wherein a gene for a targeting envelope protein is cloned into said SNV retroviral vector, said targeting envelope protein is expressed on a surface of said retroviral vector particles', said targeting envelope protein binds to a receptor on a target cell for cell-typc specific gene transfer into non-dividing cells and wherein said retroviral vector particles contain at least one SNV retroviral vector composing a nuclear localization sequence introduced into a matrix protein at a position homologous to that in HIV-1.

4. A method of introducing into a mammal at least one retroviral vector particle, wherein said particle contains an SNV retroviral vector comprising a nuclear translocation sequence introduced into a matrix protein and an SNV-derived retroviral vector comprising at least one gene to be transferred into a non-dividing cell(s) and wherein said particle further comprises a targeting envelope on said retroviral vector particles surface for specific infection of said non-dividing cell(s) in said mammal, thereby transducing said gene into said non-dividing cells in said mammal.

* * * * *